US007670807B2

(12) United States Patent
Lampson et al.

(10) Patent No.: US 7,670,807 B2
(45) Date of Patent: Mar. 2, 2010

(54) **RNA-DEPENDENT DNA POLYMERASE FROM *GEOBACILLUS STEAROTHERMOPHILUS***

(75) Inventors: Bert C. Lampson, Johnson City, TN (US); Jashree Velore, Kingsport, TN (US)

(73) Assignee: East Tennessee State Univ. Research Foundation, Johnson City, TN (US)

( * ) Notice: Subject to any disclaimer, the term of this patent is extended or adjusted under 35 U.S.C. 154(b) by 1160 days.

(21) Appl. No.: 10/797,262

(22) Filed: Mar. 10, 2004

(65) Prior Publication Data

US 2010/0003723 A1 Jan. 7, 2010

(51) Int. Cl.
*C12N 9/12* (2006.01)
*C12P 19/34* (2006.01)

(52) U.S. Cl. ...................... 435/91.1; 435/194; 435/183; 530/350

(58) Field of Classification Search ....................... None
See application file for complete search history.

(56) References Cited

U.S. PATENT DOCUMENTS 7,094,539 B2 * 8/2006 Gu et al. ........................ 435/6

OTHER PUBLICATIONS

Ngo et al., in The Protein Folding Problem and Tertiary Structure Prediction, 1994, Merz et al. (ed.), Birkhauser, Boston, MA, pp. 433 and 492-495.*

*Biokhimiia*, Apr. 1981, vol. 46(4): 681-90 (Abstract from PubMed: PMID 7284483); "Isolation and Properties of Two DNA-Polymerases from *Bacillus stearothermophilus* Cells".

*Journal of Bacteriology*, Jan. 1981, vol. 145 (1): 21-26, American Society for Microbiology, Washington, D.C.; "Purification and Properties of Deoxyribonucleic Acid Polymerase from *Bacillus stearothermophilus*".

*Journal of Bacteriology*, Jul. 1992, vol. 174 (13): 4350-4355, American Society for Microbiology, Washington, D.C.; "Purification and Characterization of DNA Polymerases from *Bacillus* Species".

* cited by examiner

*Primary Examiner*—Richard G Hutson
(74) *Attorney, Agent, or Firm*—Donna J. Russell

(57) ABSTRACT

The invention relates to an isolated polynucleotide sequence from the genome of *Bacillus stearothermophilus* (*Geobacillus stearothermophilus*) and an amino acid sequence encoded by the polynucleotide sequence, the corresponding amino acid sequence comprising a novel enzyme, Tirt (thermostable intron reverse transcriptase), having reverse transcriptase activity and retaining that activity at temperatures of up to about 75° C.

11 Claims, 8 Drawing Sheets

Fig. 1

```
                        1             15 16            30 31            45 46            60 61            75 76            90
1 B.halodurans          --------------- --------------- --------------- ---------MLERIL SRENLIQALERVEKN KGSYGVDEMDVKSLR 36
2 C.acetobutylicum      -MKNSKEMQKLQTTS YKEGWSCEIRVELQN STRAHSISTAFDRRK DDGKLYETNLLERIL DRQNMNLAYKRVKSN KGSHGVDGMKVDELL 89
3 Bst803-2065           --------------- --------------- --------------- -------MALLERIL ARDNLITALKRVEAN QGAPGIDGVSTDQLR 38
4 PalcaligenesMatur     MPPVGVAVSLVTVMQ KFPTAETVIPNPGQK PRVMPDSAKVPAASA TWTNAEPDTLMERVL APANLRRAYQRVVSN KGAPGADGMTVADLA 90

                        91           105 106          120 121          135 136          150 151          165 166          180
1 B.halodurans          LHLHENWTSIRNEII EGSYFPKPVRRVEIP KPNGGVRKLGIPTVM DRFLQQAIAQILTQL YDPTFSERSFGFRPH RRGHNAVRQAKQWMK 126
2 C.acetobutylicum      QYLKQNGKTLIASIF NGKYCPKAVRRVEIP KPDGGIRLLGIPTVV DRTIQQAISQVLTPI FEKTFSENSYGFRPK RSAKQAIKKAKEYME 179
3 Bst803-2065           DYIRAHWSTIRAQLL AGTYRPAPVRRVGIP KPGGGTRQLGIPTVV DRLIQQAILQELTPI FDPDFSPSSFGFRPG RNAHDAVRQAQGYIQ 128
4 PalcaligenesMatur     GYVKQYWPTLKARLL AGEYHPQAVRAVEIP KPQGGTRQLGIPSVV DRLIQQALQQQLTPI FDPLFSDYSYGFRPG RSTHQAIEMARAHVT 180
                                                   I            II

                        181          195 196          210 211          225 226          240 241          255 256          270
1 B.halodurans          EGYRWVVDIDLEKFF DKVNHDRLMRKLSSR IQDPRVLQLIRRYLQ TGVMERGLVSPNTEG TPQGGPLSPLLSNIV LDELDNELEKRGLKF 216
2 C.acetobutylicum      EGYKWVVDIDLAKYF DTVNHDKLMALVARK IKDKRVLKLIRLYLQ SGVMINGVVSETERG CPQGGPLSPLLSNIM LTELDRELEKRGHKF 269
3 Bst803-2065           EGYRYVVDMDLEKFF DRVNHDILMSRVARK VKDKRVLKLIRAYLQ AGVMIEGVKVQTEEG TPQGGPLSPLLANIL LDDLDKELEKRGLKF 218
4 PalcaligenesMatur     AGHRWCVELDLEKFF DRVNHDILMACIERR IKDKCVLRLIRRYLE AGIMSGGVVSPRQEG TPQGGPLSPLLSNIL LDELDRELERRGHRF 270
                               III                                                         IV

                        271          285 286          300 301          315 316          330 331          345 346          360
1 B.halodurans          VRYADDCNIYVRSKR AGLRIMESVTSFIEN RLKLKVNREKSAVDR PWNRKFLGFSFTRGK -DPKMRVSKESVKRL KQRIRELTSRRHSMK 305
2 C.acetobutylicum      CRYADDNNVYVRSKK AGDRVMRSITRFIEN KLKLKVNKEKSAVDR PWRRKFLGFTFYQPY GKIGIRVHEKSVKKF KAKIKAITARSNALN 359
3 Bst803-2065           CRYADDCNIYVKSLR AGQRVKQSIQRFLEK TLKLKVNEEKSAVDR PWKRAFLGFSFTPER -KARIRLAPRSIQRL KQRIRQLTNPNWSIS 307
4 PalcaligenesMatur     VRYADDANIYVRSPR AGERVLVSVERFLRE RLKLTVNRKKSQVAR AWKCDYLGYGMSWHQ -QPRLRVARMSLDRL RDRLRMLLRSVRARK 359
                          V                          VI                   VII                -------------------

                                  LN  G    YY
                        361          375 376          390 391          405 406          420 421          435 436          450
1 B.halodurans          MSDRLRRLNRYLTGW LGYYQVVDTPSILAQ IDAWIRRRLRMIRWK EWKTTSARQKNLVRL GIKKAKAWQWANSRK GYWRVAHSPIMDYAL 395
2 C.acetobutylicum      IENRIIKLRQCIIGW LNYFGIAEMTKLAKK LDEWTRRRLRMCYWK QWKKVKTKYDNLRKF GINNSKAWEFANTRK SYWRIANSPILSTTL 449
3 Bst803-2065           MPERIHRVNQYVMGW IGYFRLVETPSVLQT IEGWIRRRLRLCQWL QWKRVRTRIRELRAL GLKETAVMEIANTRK GAWRTTKTPQLHQAL 397
4 PalcaligenesMatur     MATVIERINPVLRGW ASYFKLSQSKRPLEE LDGWVRHKLRCVIWR QWKQPPTRLRNLMRL GLSEERANKSAFNGR GPWWNSGAQHMNYAL 449
                        ---------------------------------------
                                    "X" Domain
```

1 - SEQ ID NO: 13 2 - SEQ ID NO: 14 3 - SEQ ID NO: 2 4 - SEQ ID NO: 15

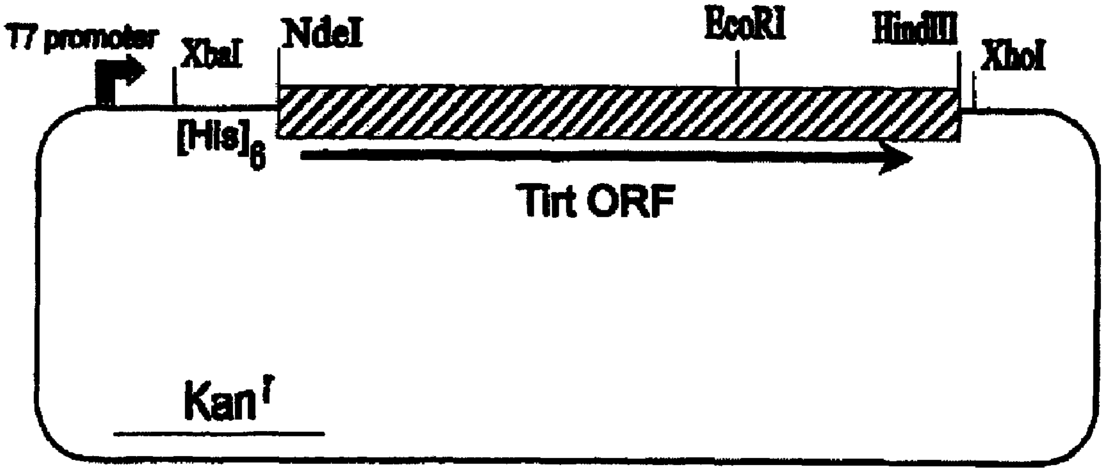

Plasmid pTirt#16

B.

```
                                               T7 promoter
  1 TGGNNNNAGT NTTTAAACCT TTGNACCGCC NTAATACNAC TCACTATAGG
     lac operator
 51 GGAATTGTGA GCGGATAACA ATTCCCCTCT AGAAATAATT TTNTTTAACT
          rbs                                His-tag
101 TTAAGAAGGA GATATACCat gggcagcagc catcatcatc atcatcacag
                         M  G  S  S  H  H  H  H   H  H  S
                        > start of fusion  NdeI
151 cagcggcctg gtgccgcgcg gcagccatat gcggcaagac ctgaatctca
     S  G  L   V  P  R  G   S  H  M   R  Q  D   L  N  L  I

201 tcccgcggaa ggagaagatc acgatggctt tgttggaacg catcttagcg
      P  R  K   E  K  I   T  M  A  L   L  E  R   I  L  A
                              > start of Tirt ORF
251 agagacaacc tcatcacggc gctcaaacgg gtcgaagcca accaaggagc
     R  D  N  L   I  T  A   L  K  R   V  E  A  N   Q  G  A
```

DNA Sequence - SEQ ID NO: 17

Amino Acid Sequence - SEQ ID NO: 18

RNA-DEPENDENT DNA POLYMERASE FROM *GEOBACILLUS STEAROTHERMOPHILUS*

FIELD OF THE INVENTION

The present invention relates to DNA and protein sequences encoding heat-stable polymerase enzymes, expression vector constructs for recombinant production of such enzymes, and methods of use for heat-stable polymerases. More specifically, the invention relates to a substantially pure thermostable RNA-directed DNA polymerase (i.e., reverse transcriptase) isolated from *Geobacillus stearothermophilus*. The invention also relates to the cloning and expression of the *G. stearothermophilus* RNA-directed DNA polymerase in *Escherichia coli*, to DNA molecules containing the cloned gene, and to hosts which express said genes.

BACKGROUND OF THE INVENTION

Heat-stable enzymes are essential tools of molecular biology that have proven invaluable in DNA cloning, sequencing, and random mutagenesis. The most often used heat-stable polymerases are the DNA polymerases utilized in polymerase chain reactions (PCR) reactions. These are often coupled with reverse transcriptases in RT-PCR, when an RNA molecule is used as a template to form a complementary DNA (cDNA) molecule, and that cDNA sequence is amplified by polymerase chain reaction (PCR). cDNA synthesis is most often done using reverse transcriptase enzymes of viral origin, with the reactions being performed at temperatures below about 50° C., which is optimal for these enzymes. There are, however, distinct advantages to synthesizing cDNA at temperatures above 50° C., since higher temperatures melt the secondary structures that can form in the RNA template and block further processivity of the transcriptase enzyme. A reverse transcriptase that remains stable and active at higher temperatures is especially useful for cDNA synthesis in combination reverse transcription/polymerase chain reaction (RT-PCR) reactions, as well as in other applications. Since higher temperatures can eliminate the secondary structures that may form in the RNA template, the length of the cDNA product can be extended. Higher temperatures also reduce the amount of non-specific annealing of PCR primers during cDNA synthesis, increasing specificity and amplification of cDNA. Higher temperatures can also melt the 3' end of a mismatched primer, inhibiting further synthesis from the primer and limiting incorporation of mismatched bases in the cDNA product.

Retroviral reverse transcriptases generally have three potential enzymatic activities associated with them: an RNA-directed DNA polymerase, a DNA-directed DNA polymerase, and an RNAse H activity. Therefore, when retroviral RTs are used to copy RNA or DNA, an RNAse inhibitor must often be included in the reaction to minimize RNAse effects. Unfortunately, this can also inhibit the action of other enzymes. Furthermore, retroviral enzymes are typically most effective at temperatures at or below 50° C.

To produce cDNA at higher temperatures, a DNA-dependent, DNA polymerase Tth pol, from the thermophilic bacterium *Thermus thermophilus*, has been used. Although it is not technically classified as a reverse transcriptase, it will reverse transcribe RNA at high temperatures in an RT-PCR reaction. Manganese chloride ($MnCl_2$) must be added to the reaction to boost efficiency, but this also reduces the fidelity of cDNA synthesis so that an added step is necessary to remove it prior to PCR amplification.

An RNase H-deficient Avian Myeloblastosis Virus reverse transcriptase (AMV-RT) has been used in RT-PCR reactions, the RNase H-deficient enzyme being more thermostable than the native enzyme. This RT does not degrade the RNA template, increasing the amount of full-length cDNA product that can be produced. cDNA synthesis with this enzyme is generally performed at 50° C., but larger amounts of the enzyme and substrate dNTPs are required for cDNA synthesis at higher temperatures, and synthesis from long RNA templates is often truncated, even at the higher temperature. AMV-RT also comprises two polypeptide chains (α and β), making it more difficult and expensive to produce as a recombinant product. When expressed in *E. coli*, for example, the end product is not appropriately modified to provide a fully active enzyme. An RT from Moloney Murine Leukemia Virus (MMLV) is also commercially available for use in reverse transcription reactions. Invitrogen's (Carlsbad, Calif.) SuperscriptII® RT is a point mutant of M-MLV-RT. According to the product literature, SuperscriptII® RT can be used at temperatures up to 50° C., and native M-MLV-RT can be used at temperatures up to 42° C.

Although there are currently enzymes which can be used in RT-PCR and other similar types of reactions, there is still a significant need for an improved RT that remains active, accurate, and stable at high temperatures and can be used in a one-step reaction system for RT-PCR.

SUMMARY OF THE INVENTION

The present invention relates to a novel isolated polynucleotide sequence from the genome of *Bacillus stearothermophilus* (*Geobacillus stearothermophilus*) SEQ ID NO 1, and a novel amino acid sequence (SEQ ID NO 2) encoded by the polynucleotide sequence, the corresponding amino acid sequence comprising a heat-stable protein with reverse transcriptase activity. The invention provides a novel enzyme, Tirt (thermostable intron reverse transcriptase), which has reverse transcriptase activity and retains that activity at temperatures of up to about 75° C.

The invention further relates to a method of using such a reverse transcriptase enzyme to facilitate DNA cloning, and at least one type of kit with prepared reagents to perform the necessary reactions for RT-PCR. The invention also provides a method of performing reverse transcription of an RNA sequence to form a cDNA sequence, and further provides a method for performing RT-PCR with the reverse transcription reaction being performed at temperatures elevated to about 75° C.

BRIEF DESCRIPTION OF THE DRAWINGS

FIG. 1 is a multiple amino acid sequence alignment comparison of the Tirt sequence with group II intron-encoded ORFs. The open reading frame (ORF) designated Bst 803-2065 encodes the Tirt protein and was cloned from the genome of *G. stearothermophilus* strain 10. The amino acid sequence of Tirt is compared with the amino acid sequence from three related ORFs encoded by group II introns from bacteria. These sequences include an ORF from *Bacillus halodurans* (ATCC accession no. NC002570.1), an RT-maturase protein from *Clostridium acetobutylicum* (ATCC accession no. NC003030), and a group II intron protein from *Pseudomonas alcaligenes* (ATCC accession no. U77945). Common to RTs, the Tirt sequence contains most of the highly conserved amino acids that fall into seven distinct domains (underlined sequences lableled I-VII). These seven conserved domains correspond to important structural regions proposed to be shared by all RTs. In addition, the Tirt sequence also contains most of the highly conserved amino acids contained in a region of the protein designated "X". This domain is associated with the maturase function of group II intron encoded proteins. The most conserved amino acids found in the "X" region of bacterial group II intron proteins (according to Zimmerly et al. *Nucleic Acids Res.* (2000) 29: 1238-1250) are shown above the alignment in italics.

FIG. 8. is a map of the pTirt#16 plasmid, for the over-expression and purification of the Tirt protein. (A) The restriction endonuclease map of plasmid pTirt# 16 indicates the location of the genomic DNA (hatched rectangle) cloned from *G. stearothermophilus* that contains the Tirt ORF. The Tirt ORF was cloned adjacent to a T7 promoter and in frame with a poly-histidine ($[HiS]_6$) tag to allow over-expression of the Tirt protein and simplify purification. (B) A partial DNA sequence of the pTirt#16 plasmid shows the junction region where the Tirt ORF is fused in frame with the poly-histidine tag element (underlined sequence) down stream of the T7 promoter, creating a 35 amino acid extension at the N-terminus of the Tirt ORF that includes six consecutive histidine amino acids.

DETAILED DESCRIPTION

The present invention seeks to overcome the shortcomings of the prior art by providing a thermostable RNA-directed DNA polymerase as found in the thermophilic bacterium *Geobacillus stearothermophilus* (also known as *Bacillus stearothermophilus*). Geobacillus stearothermophilus is an organism isolated from the formation waters of Russian oil-fields. A DNA-dependent DNA polymerase from this organism has previously been described. The inventors describe here the discovery of a functional RNA-dependent DNA polymerase enzyme encoded within the genome of *G. stearothermophilus*. While investigating putative coding regions within the sequence data, the inventors discovered a sequence having characteristics similar to those of type II introns, which have reverse transcriptase activity. In methods to be described herein, the inventors isolated DNA encoding a protein they have designated as Tirt (for "thermostable intron reverse transcriptase"), constructed an expression vector for its overexpression, and demonstrated that it has reverse transcriptase activity even after being heated to about 75° C.

Figure 2:
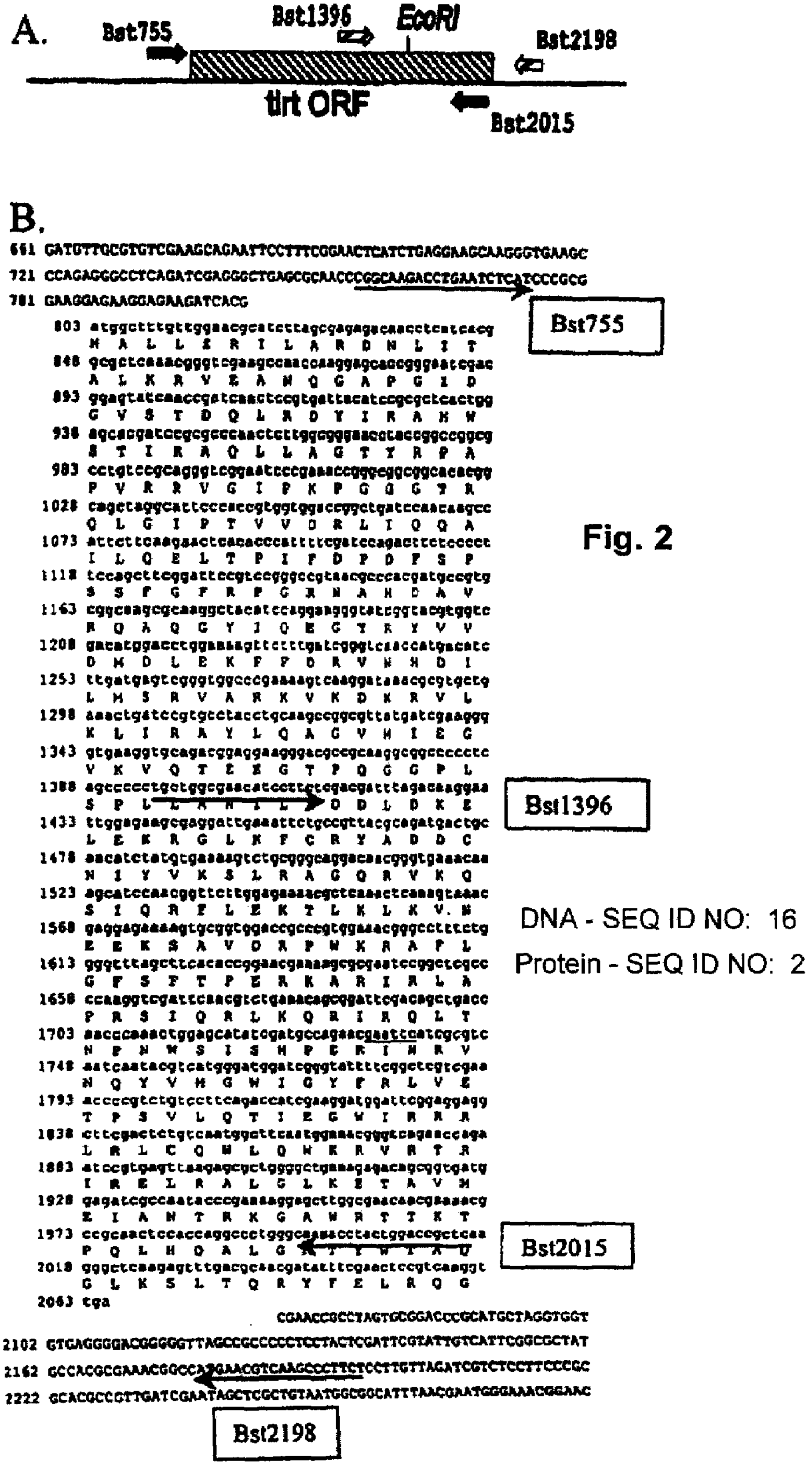
FIG. 2 is the polynucleotide sequence of the tirt ORF from *G. stearothermophilus*. The location of DNA sequences used to design the primers Bst755, Bst1396, Bst2015, and Bst2198 are shown by the designated arrows. These primers were used to amplify the tirt-ORF for cloning.

The DNA sequence shown in FIG. 2 is from the incomplete genomic DNA sequence of *Bacillus* (*Geobacillus*) *stearothermophilus* strain 10 obtained from the Genome Sequencing Project, Advanced Center for Genome Technology, University of Oklahoma (Experimental Program to Stimulate Competitive Research Grant #EPS-9550478). The inventors have discovered that the sequence encodes a 420-amino acid ORF containing the Tirt protein.

Retroelements are genetic elements that code for a reverse transcriptase and employ the process of reverse transcription in some stage of their replication or mobility. A large variety of these retroelements are found in nearly every type of eukaryotic organism. They include some RNA viruses, DNA viruses, transposons, introns, and even mitochondrial plasmids. Bacteria also contain RT-encoding genetic elements (retro-elements) that fall into two basic types. The group II introns, found in a variety of bacteria, contain a reverse transcriptase region as part of the intron-encoded ORF. A retron, on the other hand, produces an unusual satellite DNA called msDNA. The inventors compared the amino acid sequence from ten different retron RTs with the amino acid sequence from five different bacterial group II intron ORFs by multiple sequence alignment (Clustal W alignment). They then used the multiple sequence alignment to generate a consensus amino acid sequence for RTs found in bacteria. The bacterial consensus sequence was used as the query sequence in a BLAST search of both the GenBank database as well as the bacterial genomes database that contains both completed, as well as, unfinished bacterial species. These searches revealed several ORFs with similarity to the consensus sequence that had not been previously described. This included a 420-amino acid ORF from the unfinished genome sequence of *G. stearothermophilus.*

The amino acid sequence of this *G. stearothermophilus* ORF was further analyzed by comparison with other RTs and found to be strongly similar to group II intron ORFs from both bacteria and mitochondria (FIG. 1). The amino acid sequences of RTs are generally highly variable. However, multiple amino acid sequence alignments demonstrate the presence of a few highly conserved amino acids shared among all RTs. These conserved amino acids fall into seven domains (designated I-VII, FIG. 1) that correspond to conserved secondary structures within the folded RT protein. A short distance beyond domain VII is an additional conserved region designated domain "X", that is found only in group II intron encoded proteins. Domain X is associated with the maturase function found in group II intron ORFs. Although domain X is not well conserved among bacterial group II intron proteins, the *G. stearothermophilus* ORF appears to contain most of the conserved amino acids of domain X shared among bacterial group II introns (FIG. 1). Thus, the *G. stearothermophilus* ORF appears to have most of the highly conserved amino acids present in both the RT region and the maturase region (or domain X) of group II intron proteins (FIG. 1). For this reason the *G. stearothermophilus* ORF is clearly not a retron type RT and was thus designated tirt for thermostable intron reverse transcriptase. Some proteins encoded by group II introns also contain a third, zinc finger domain that imparts an endonuclease activity on this multifunctional protein. However, based on sequence comparisons, this endonuclease domain appears to be absent from the tirt ORF.

As used herein, the term "protein" is intended to include mimetics and the term "amino acid" is intended to include L-form, D-form, and modified amino acids. These substitutions may be made by someone of skill in the art, using the known structural similarities between the molecules. The amino acid sequence is also intended to include any peptide or protein sequence that may include additional amino acids either N-terminal or C-terminal to the listed sequence, or both. The term "Tirt protein" is intended to include variants or biologically active fragments of the polypeptide.

It is well known in the art that a single amino acid may be encoded by more than one nucleotide codon, and that the nucleotide sequence may be modified to produce an alternate nucleotide sequence that encodes the same peptide. Therefore, alternate embodiments of the present invention include alternate DNA sequences encoding peptides containing the amino acid sequences as previously described. DNA sequences encoding peptides containing the claimed amino acid sequence include DNA sequences which encode any combination of the claimed sequence and any other amino acids located N-terminal or C-terminal to the claimed amino acid sequence.

It is to be understood that amino acid and nucleic acid sequences may include additional residues, particularly N- or C-terminal amino acids or 5' or 3' nucleotide sequences, and still be essentially as set forth in the sequences disclosed herein, as long as the sequence confers heat-stable RNA-dependent DNA polymerase activity upon the polypeptide or protein moiety of the expressed protein.

Additional nucleic acid bases may be added either 5' or 3' to the Tirt ORF, and may be combined with other DNA sequences, such as promoters, polyadenylation signals, additional restriction enzyme sites, multiple cloning sites, other coding segments, and the like. Therefore, overall length of such a polynucleotide may vary considerably. In a method described by the present invention, a nucleotide sequence as shown in FIG. 2 is inserted into a protein expression vector to produce a protein which can be used to synthesize a DNA copy of an RNA molecule. The DNA can then be amplified to form multiple copies, at temperatures elevated to about 68 to about 75 degrees Celsius.

"Control sequences" are those DNA sequences that are necessary for the expression of a protein from a polynucleotide sequence containing such a sequence, operably linked to the polynucleotide sequence encoding the protein. These sequences include prokaryotic sequences such as, for example, promoters, operators, and ribosome binding sites, and eukaryotic sequences such as, for example, promoters, enhancers, and polyadenylation signals. "Expression systems" are DNA sequences (such as, for example, plasmids) appropriate for expression of a target protein in a particular host cell, these sequences comprising appropriate control sequences for protein expression in the host cell operably linked to the polynucleotide sequence encoding the target protein.

It is to be understood that a "variant" of a polypeptide is not completely identical to the native protein. A variant Tirt protein, for example, can be obtained by altering the amino acid sequence by insertion, deletion or substitution of one or more amino acids. The amino acid sequence of the protein can be modified, for example, by substitution to create a polypeptide having substantially the same or improved qualities as compared to the native polypeptide. The substitution may be a conserved substitution. A "conserved substitution" is a substitution of an amino acid with another amino acid having a side chain that is similar in polar/nonpolar nature, charge, or size. The 20 essential amino acids can be grouped as those having nonpolar side chains (alanine, valine, leucine, isoleucine, proline, phenylalanine, and tryptophan), uncharged polar side chains (methionine, glycine, serine, threonine, cystine, tyrosine, asparagine and glutamine), acidic side chains (aspartate and glutamate), and basic side chains (lysine, arginine, and histidine). Conserved substitutions might include, for example, Asp to Glu, Asn, or Gln; H is to Lys, Arg or Phe;

Asn to Gin, Asp or Glu; and Ser to Cys, Thr or Gly. Alanine, for example, is often used to make conserved substitutions.

To those of skill in the art, variant polypeptides can be obtained by substituting a first amino acid for a second amino acid at one or more positions in the polypeptide structure in order to affect biological activity. Amino acid substitutions may, for example, induce conformational changes in a polypeptide that result in increased biological activity.

Those of skill in the art may also make substitutions in the amino acid sequence based on the hydrophilicity index or hydropathic index of the amino acids. A variant amino acid molecule of the present invention, therefore, has less than one hundred percent, but at least about fifty percent, and preferably at least about eighty to about ninety percent amino acid sequence homology or identity to the amino acid sequence of a polypeptide comprising SEQ ID NO 2, or a polypeptide encoded by SEQ ID NO 1. Therefore, the amino acid sequence of the variant Tirt protein corresponds essentially to the native Tirt protein amino acid sequence. As used herein, "corresponds essentially to" refers to a polypeptide sequence that will elicit a similar biological and enzymatic activity to that generated by a Tirt protein comprising SEQ ID NO 2, such activity being at least about 70 percent that of the native Tirt protein, and more preferably greater than 100 percent of the activity of the native Tirt protein.

A variant of the Tirt protein may include amino acid residues not present in a corresponding Tirt protein comprising SEQ ID NO 2, or may include deletions relative to the Tirt protein comprising SEQ ID NO 2. A variant may also be a truncated "fragment," as compared to the corresponding protein comprising SEQ ID NO 2, the fragment being only a portion of the full-length protein.

In a preferred embodiment of the present invention, a protein expression vector is genetically engineered to incorporate a DNA sequence encoding the Tirt ORF and appropriate control sequences comprising, for example, transcriptional and translational sequences such as promoter and polyadenylation sequences, to produce a functional Tirt protein.

The isolated polynucleotide and protein of the present invention can be used in a variety of applications, including, but not limited to assays to confirm the presence of viral infection in tissue samples, preparation of cDNA copies of isolated or cellular RNAs, and real-time or standard RT-PCR for genetic analysis. These and other uses known to, or developed by, those of skill in the art are made possible by the discovery of the thermostable intron reverse transcriptase of the present invention.

Expression vectors may be chosen from among those readily available for prokaryotic or eukaryotic expression systems. Expression system vectors, which incorporate the necessary regulatory elements for protein expression, as well as restriction endonuclease sites that facilitate cloning of the desired sequences into the vector, are known to those of skill in the art. A number of these expression vectors are commercially available. In one preferred embodiment of the present invention, the expression vector is pET28 (Novagen, Madison, Wis.).

An expression vector host cell system can be chosen from among a number of such systems that are known to those of skill in the art. In one embodiment of the invention, the protein can be expressed in *E. coli*. In alternate embodiments of the present invention, the enzyme may be expressed and purified using other bacterial expression systems, viral expression systems, eukaryotic expression systems, or cell-free expression systems. Cellular hosts used by those of skill in the art for expression of various proteins include, but are not limited to, *Bacillus subtilis*, yeast such as *Saccharomyces cerevisiae, Saccharomyces carlsbergenesis, Saccharomyces pombe*, and *Pichia pastoris*, as well as mammalian cells such as 3T3, HeLa, and Vero. The expression vector chosen by one of skill in the art will include promoter elements and other regulatory elements appropriate for the host cell or cell-free system in which the recombinant DNA sequence encoding the enzyme will be expressed. In mammalian expression systems, for example, suitable expression vectors can include DNA plasmids, DNA viruses, and RNA viruses. In bacterial expression systems, suitable vectors can include plasmid DNA and bacteriophage vectors.

One group of vectors that can be used to express and facilitate purification of the protein include those vectors that encode the polyhistidine (6xHis) sequence and an epitope tag to allow rapid purification of the fusion protein with a nickel-chelating resin, along with protein detection with specific antibodies to detect the presence of the secreted protein. An example of such a vector for expression in mammalian cells is the pcDNA3.1/V5-His-TOPO eukaryotic expression vector (Invitrogen). In this vector, the fusion protein can be expressed at high levels under the control of a strong cytomegalovirus (CMV) promoter. A C-terminal polyhistidine (6xHis) tag enables fusion protein purification using nickel-chelating resin. Secreted protein produced by this vector can be detected using an anti-His (C-term) antibody.

Since Tirt is a bacterial protein, bacterial expression systems are particularly suited for expression of the Tirt protein as described by the present invention. Such systems include, for example, the pMAL system (New England Biolabs, Beverly, Mass.) which utilizes a maltose binding protein fusion to facilitate purification, and the Impact-CN Protein Fusion and Purification System (New England Biolabs).

A baculovirus expression system can be used for production of a target protein such as the enzyme of the present invention. A commonly used baculovirus is AcMNPV. Cloning of the target protein DNA can be accomplished by using homologous recombination. The target protein DNA sequence is cloned into a transfer vector containing a baculovirus promoter flanked by baculovirus DNA, particularly DNA from the polyhedrin gene. This DNA is transfected into insect cells, where homologous recombination occurs to insert the target protein into the genome of the parent virus. Recombinants are identified by altered plaque morphology.

Proteins as described above can also be produced in the method of the present invention by mammalian viral expression systems. The Sindbis viral expression system, for example, can be used to express proteins at high levels. Sindbis vectors have been described, for example, in U.S. Pat. No. 5,091,309 (Schlesinger et al.), incorporated herein by reference. Sindbis expression vectors, such as pSinHis (Invitrogen, Carlsbad, Calif.) can be used to express the Tirt protein under the direction of the subgenomic promoter PSG. In vitro transcribed RNA molecules encoding the fusion protein and the Sindbis proteins required for in vivo RNA amplification can be electroporated into baby hamster kidney (BHK) cells using methods known to those of skill in the art. Alternatively, the RNA encoding the Tirt protein and Sindbis proteins required for in vivo RNA amplification can be cotransfected with helper RNA that permits the production of recombinant viral particles. Viral particles containing genetic material encoding the fusion protein can then be used to infect cells of a wide variety of cell types, including mammalian, avian, reptilian, and *Drosophila*. Fusion protein expressed from the pSinHis (Invitrogen) vector can be detected with antibody to an Anti-Xpress™ epitope encoded by the vector sequence. The pSinHis vector also includes a polyhistidine tag which provides a binding site for metal-chelating resins to facilitate purification of the expressed fusion protein. Furthermore, an enterokinase cleavage site located between the histidine tag and the fusion protein allows the histidine tag to be enzymatically removed following purification.

An ecdysone-inducible mammalian expression system (Invitrogen, Carlsbad, Calif.) can also be used to express a target protein. Vectors used in the ecdysone-inducible mammalian expression system can be organized to produce the target protein by expressing the target protein from the expression cassette. With the ecdysone-inducible system, higher levels of protein production can be achieved by use of the insect hormone 20-OH ecdysone to activate gene expression via the ecdysone receptor. An inducible expression plasmid provides a multiple cloning site, into which the nucleotide sequence of the Tirt protein can be ligated. The expression vector contains ecdysone response elements upstream of the promoter (a minimal heat shock promoter) and the multiple cloning site. Cotransfection of a second plasmid, pVgRXR (Invitrogen), provides the receptor subunits to make the cell responsive to the steroid hormone ecdysone analog, ponasterone A. A control expression plasmid containing the lacZ gene can be cotransfected with pVgRXR to provide a marker for transfected cells. Upon induction with ponasterone A, the control plasmid expresses β-galactosidase. Cotransfection of the inducible expression construct and pVgRXR into the mammalian cell of choice can be accomplished by any of the standard means known to those of skill in the art. These include, for example, calcium phosphate transfection, lipid-mediated transfection, and electroporation. Levels of expression of the fusion protein in this system can be varied according to the concentration and length of exposure to ponasterone. Stable cell lines that constitutively express the Tirt protein can be established using Zeocin™ (Invitrogen), a bleomycin/phleomycin-type antibiotic isolated from *Streptomyces*, and neomycin or hygromycin.

Yeast host cells, such as *Pichia pastoris*, can also be used for the production of the Tirt protein. Expression of heterologous proteins from plasmids transformed into *Pichia* has previously been described by Sreekrishna, et al. (U.S. Pat. No. 5,002,876, incorporated herein by reference). Vectors for expression in *Pichia* of a Tirt protein are commercially available as part of a Pichia Expression Kit (Invitrogen, Carlsbad, Calif.). *Pichia pastoris* is a methylotrophic yeast, which produces large amounts of alcohol oxidase to avoid the toxicity of hydrogen peroxide produced as a result of methanol metabolism. Alcohol oxidase gene expression is tightly regulated by the AOX1 and AOX2 promoters. In *Pichia* expression vectors, high levels of expression are produced under the control of these promoters. Ohi, et al. (U.S. Pat. No. 5,683,893, incorporated herein by reference) have previously described a mutant AOX2 promoter capable of producing enhanced expression levels.

PCR primers were designed based on the DNA sequence recovered from a BLAST search of the unfinished genome sequence of *G. stearothermophilus* from the "BLAST with bacterial genomes" web page at the National Center for Biotech Information (www.ncbi.nlm.nih-gov/blast) (see FIG. 1). The program Primer3 (available at the web site: www-genome.wi.mit.edu/cgi-bin/primer/primer3) was used to aid in design of primers. The DNA sequence of plasmid pTirt#16 and other constructs was determined by BigDye terminator cycle sequencing using an ABI 327 automated DNA sequencer at the sequencing service (Molecular Biology Core facility) provided by the Quillen College of Medicine at East Tennessee State University. Multiple amino acid sequence alignments of the tirt ORF with other known intron ORFs was done using Clustal W available from the Baylor College of Medicine at http://searchlauncher.bc.tmc.edu/).

Protocols for performing reverse transcription, RT-PCR, real-time RT-PCR, real-time relative RT-PCR, construction of cDNA libraries, and competitive reverse transcriptase PCR analysis of cellular genes are known to those of skill in the art. One such protocol for competitive reverse transcriptase PCR analysis is described by Waha, et al. in *Brain Pathology*, Vol. 8 (1998), pages 13 to 18. Protocols for detecting the presence of viral infection include, for example, those described by Henrickson, et al., in U.S. Pat. Nos. 5,744,299 (parainfluenza virus type 1) and 6,014,664 (parainfluenza virus, respiratory syncytial virus, and influenza virus). More recently, detection of the Severe Acute Respiratory Syndrome (SARS) Coronavirus by real-time nested PCR following RT-PCR. (Jiang, et al, *Clin. Infectious Disease* 2004: 38 (15 Jan.) p. 293-296.) The enzyme of the present invention provides a tool for performing these protocols at higher temperatures. It is known, for example, that in the construction of cDNA libraries or in cDNA labeling, that oligo(dT) primers can be used to insure that poly(A) mRNAs are reverse transcribed, and that short random oligonucleotide primers may also be used for reverse transcription. Those of skill in the art, however, also are aware that RT reactions are often performed at approximately 42° C. in order to avoid inactivating the reverse transcriptase needed for the reaction to be catalyzed. The present invention provides an alternate enzyme for reverse transcription reactions, such as those listed above, that can be used at temperatures significantly higher than those used currently in conventional reaction systems.

The invention also provides at least one kit for performing, for example, reverse transcriptase, RT-PCR, real-time RT-PCR, competitive RT-PCR, or other protocols which rely on the presence of a reverse transcriptase, these protocols being performed at temperatures of up to about 68 to 75 degrees Celsius. Such a kit may comprise, for example, at least one reaction buffer (e.g., 50 mM Tris-pH 8.3, 100 mM KCl, and 10 mM dithiothreitol), an RNase inhibitor (to a final concentration of 10 units), NP-40 (to a final concentration of 0.17%), dNTP mix (dGTP, dCTP, dUTP, and dATP to a final concentration of 0.8 mM each), Tirt protein, Taq polymerase, BMV-RNA (as a positive control to a final concentration of 50 ng), RT primer (as a positive control primer for RT, to a final concentration of 0.02 μM), and BMV-PCR1 primer with BMV-PCR2 primer (as positive control primers for PCR, to a final concentration of 1 μM).

The present invention provides the isolated polynucleotide encoding the amino acid sequence of SEQ ID NO: 2, which can be used in production of the reverse transcriptase of the invention and the variant thereof. Furthermore, nucleic acids which hybridize with a nucleic acid encoding the amino acid sequence of SEQ ID NO: 2 under stringent conditions and encode a polypeptide having a similar reverse transcriptase activity to that of a polypeptide comprising SEQ ID NO: 2 are also included as embodiments of the present invention.

The term "stringent conditions", as used herein, means conditions in which non-specific hybridization will not generally occur. Hybridization under such conditions can be performed based on the description provided in *Molecular Cloning: A Laboratory Manual* 2nd ed., published by cold Spring Harbor Laboratory in 1989, edited by T. Maniatis et al. For example, stringent conditions include incubation with a probe in 6×SSC containing 0.5% SDS, 5×Denhardt's solution and 100 micrograms/ml salmon sperm DNA at 60° C.

The invention will be further described by means of the following non-limiting examples.

EXAMPLE 1

Cloning and Expression of the Tirt Gene

*Geobacillus stearothermophilus* strain 10 was a kind gift from Dr. Bruce Roe, University of Oklahoma, and was used for cloning the tirt gene. Cultures were grown in trypticase soy agar plates at 55° C. The plasmid pUC18 was used for routine subcloning of DNA fragments. The plasmid pET28a and the *E. coli* strain BL21(DE3) were from Novagen (Madison, Wis.) and were used for heterologous expression of the Tirt protein in *E. coli.*

While multiple sets of oligonucleotide primers were synthesized to amplify the tirt ORF, the inventors found that two pairs of primers could be used to successfully amplifying the tirt gene from the chromosome of *G. stearothermophilus*. The first primer pair, designated Bst755 and Bst2015 was used to specifically amplify most, but not all, of the tirt ORF via a simple PCR protocol (FIG. 2). A second primer pair designated Bst1396 and Bst2198 was used to amplify a region that includes the last 16 amino acids at the C-terminus of the tirt ORF (FIG. 2).

The primers used to amplify the tirt gene from the genome of *G. stearothermophilus* strain 10 comprise SEQ ID NO 4: AGACAACATATGCGGCAAGACCTGAATCTCAT-3' (with the underlined sequence indicating an NdeI restriction site for cloning into the pET28a expression vector); SEQ ID NO 5:5'-AATGGATCCGCTGGCGAACATCCTTCTC-3' (with the underlined sequence indicating a BamHI restriction site): SEQ ID NO 6:5'-ATTACTGCAGAGCGGTCCAGTAGGTTTTG-3' (with the underlined sequence indicating a PstI restriction site); and SEQ ID NO 7:5'-ACTCAAGCTTGAGAAGGGCTTGACGTTCATG-3' (with the underlined sequence indicating a HindIII restriction site for cloning into the pET28a expression vector.).

Amplification of the tirt gene was done in two stages (FIG. 2) using a single colony of *G. stearothermophilus* as a source of template. A single colony from an overnight plate culture was suspended in 10 µl of water. One µl of this cell suspension was added to a 50 µl PCR reaction mix containing 1.5 mM $MgCl_2$, Taq polymerase buffer (Promega, Madison, Wis.), 0.2 µM each dNTP, 0.5 µM each primer, and 2 units of Taq polymerase. The reaction was amplified using the following conditions: one cycle at 95° C. for 2 minutes, 30 cycles at 95° C. for one minute, 50° C. for 2 minutes, and 72° C. for 2 minutes. Amplified DNAs were purified by gel electrophoresis, digested with the appropriate restriction endonuclease and ligated into either pUC18 or directly into the pET28a expression vector. First, a 1.26 kilobase pair (Kb) amplified DNA product produced by the first primer pair (SEQ ID NO 4 and SEQ ID NO 6) was ligated into the expression plasmid pET28a. This produced an in-frame fusion between the polyhistidine tag element found in the expression plasmid and the tirt ORF. To capture the remaining 16 amino acids at the C-terminus of Tirt, a naturally occurring EcoRI site (within the tirt ORF, FIG. 2) was used to splice the 3 prime end of the PCR product produced by the second primer pair (SEQ ID NO 5 and SEQ ID NO 7) to the first amplified DNA to yield an expression plasmid, pTirt#16, containing the entire predicted ORF of the Tirt protein.

EXAMPLE 2

Expression of Tirt Protein

The plasmid pTirt#16 was used to express the Tirt protein in *E. coli* by induction of the T-7 promoter system with IPTG. Briefly, protein expression in *E. coli* was achieved using the T7 RNA polymerase system and the pET28a expression vector (Novagen, Madison, Wis.). Since the upstream primer (SEQ ID NO 4) used to amplify the tirt gene contained an NdeI restriction site, the amplified DNA containing the tirt ORF could be ligated into the NdeI restriction site of the expression vector. This produced an in-frame fusion between the polyhistidine tag element in the pET28a vector and the tirt ORF.

The Tirt fusion protein was expressed in *E. coli* strain BL21 lysogenic for µDE3. Briefly, cells of *E. coli* strain BL21(DE3) transformed with the plasmid pTirt#16 (containing the tirt fusion construct) were induced by addition of IPTG (1 mM). After 3 hours of induction, cells from a 100 ml culture were harvested and resuspended in binding buffer (1×) for nickel ion column purification (Novagen). A cell extract containing the Tirt fusion protein was prepared by incubating the cell suspension in fresh lysozyme (1 mg/ml), followed by three cycles of quick freeze-thaw (10 minutes at −80° C., followed by 10 minutes at 37° C.), followed by sonication. Centrifugation (15,000×g) and filtration (0.45µ filter) produced a cleared, crude protein preparation. The cleared extract was then loaded onto a prepared Nickel ion column (His-bind column, Novagen) and purified fractions collected according to manufacturer's instructions (Novagen).

Soluble and insoluble protein fractions were compared by resuspending cells (from a 50 ml induced culture) in one tenth volume of buffer (50 mM Tris-HCl pH 8.0, 2 mM EDTA) containing lysozyme (100 µg/ml) plus 1% triton X-100. After incubation at 30° C. for 15 minutes and sonication, the cell extract was centrifuged at 12,000×g for 15 minutes. The supernatant was mixed with an equal volume of SDS sample buffer and this served as the soluble protein fraction for protein gels. The pellet of cell debris was mixed with SDS sample buffer and this served as the insoluble protein fraction for protein gels.

Figure 3:
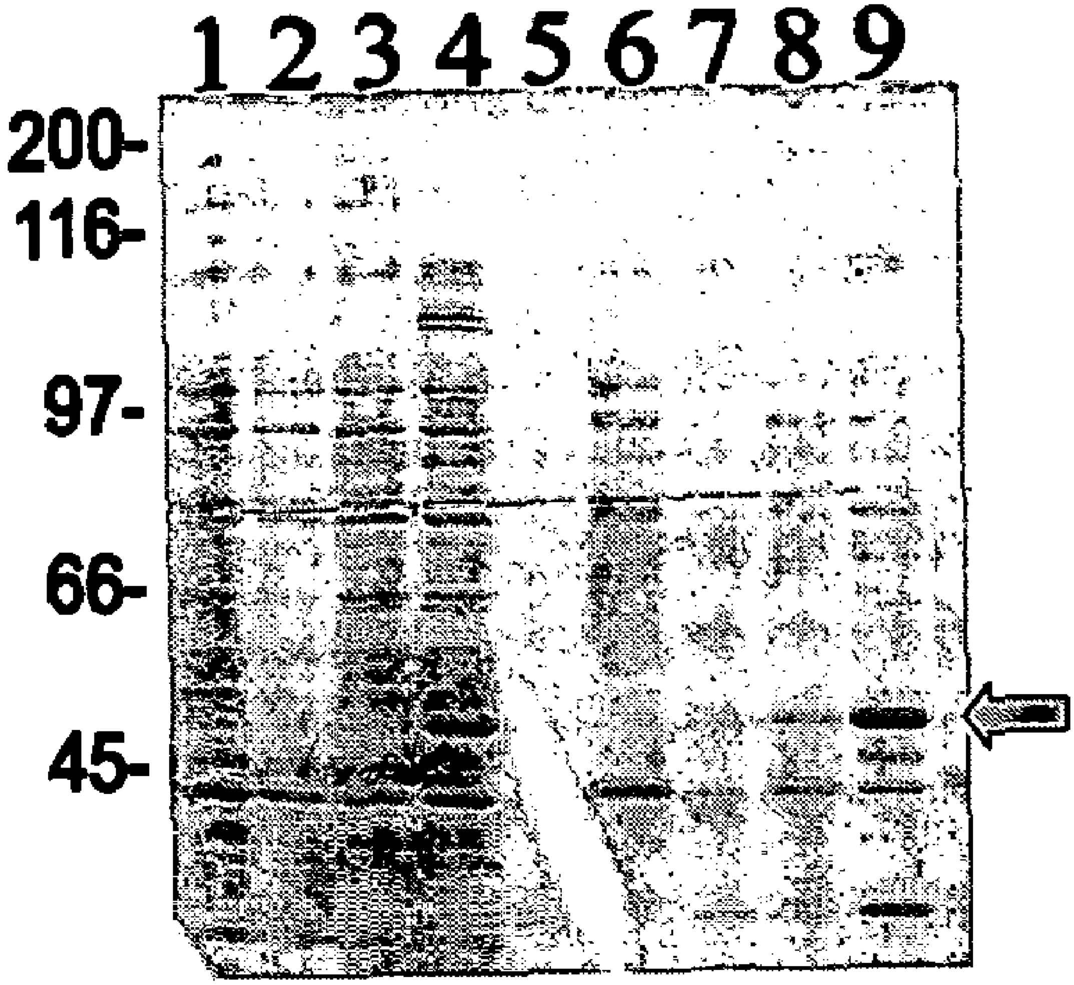
FIG. 3. is a photograph of a polyacrylamide protein gel (stained with Coomassie blue) illustrating over-expression of the Tirt fusion protein in *E. coli. E. coli* cells (BL21) containing the plasmid pTirt#16 were induced with IPTG to over-express the Tirt fusion protein via the T7 promoter system. Total protein extracts prepared from induced and non-induced cells were analyzed by polyacrylamide gel electrophoresis. A prominent protein band migrating at about 48 kD is apparent from induced cells (lane 4, indicated by arrow) but absent from non-induced cells (lane 3) and also absent from control cells containing just the plasmid vector alone (lane 1, uninduced and lane 2, induced cells). Most of the over-expressed protein band appears in the insoluble cell fraction (lane 8, soluble cell fraction versus lane 9, insoluble cell fraction). No 48 kD protein band appears in control cells containing just the expression plasmid (lane 6, soluble cell fraction and lane 7, insoluble cell fraction).
Figure 4:
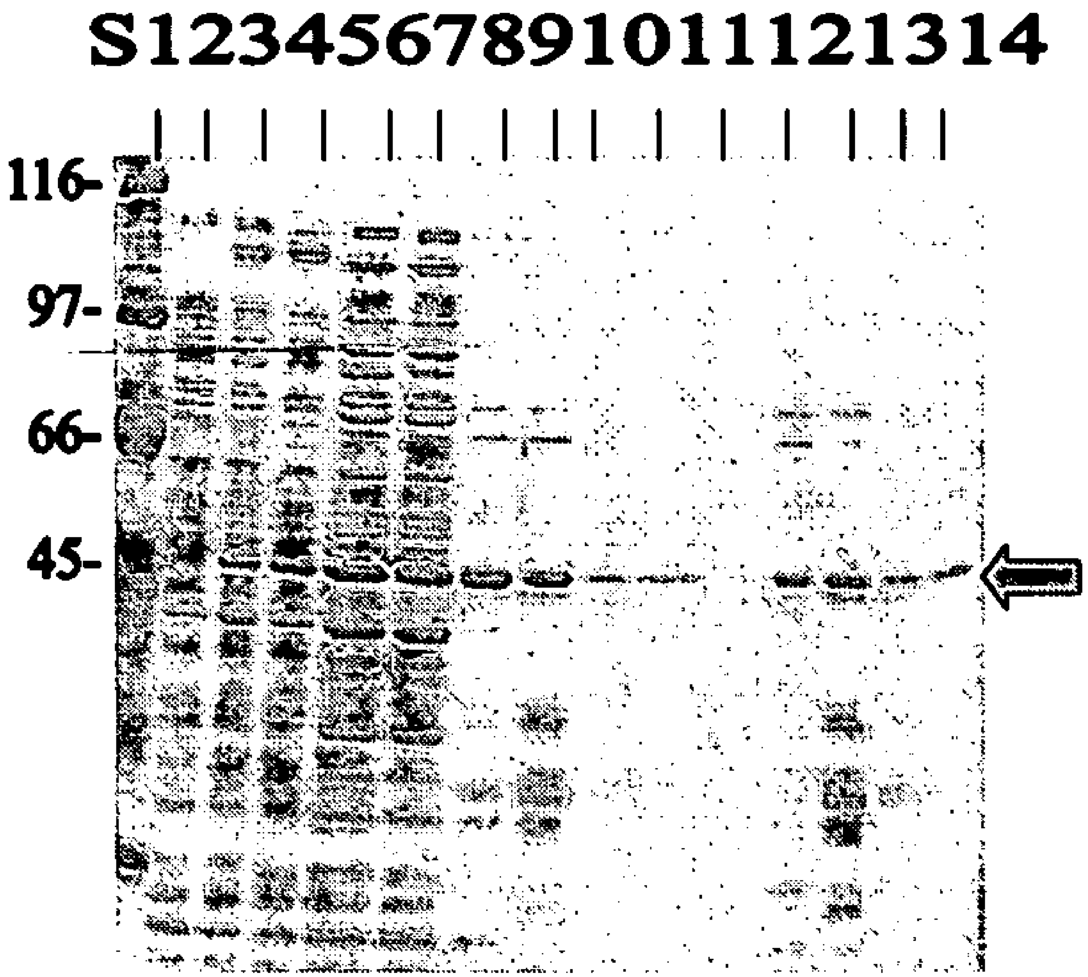
FIG. 4. is a photograph of SDS-PAGE analysis of affinity column purification of the Tirt fusion protein. The soluble fraction from a cell extract expressing the Tirt fusion protein was loaded onto a nickel ion affinity column. A single-step elution of the polyhistidine tagged fusion protein yielded a partially purified fraction containing the 48 kD protein band (arrow). Column fractions 3-6 were analyzed by electrophoresis on a polyacrylamide protein gel stained with coomassie blue (lanes 6-9, respectively). The RT activity of each column fraction was stabilized by dialysis into buffer A (lanes 11-14). Lane 3 contains the insoluble cell fraction and lane 4 contains the soluble cell fraction that was loaded onto the column. Lane 5 contains the column flow-through. Lanes 1 and 2 contain a total cell extract from uninduced and induced cells respectively. Lane S contains a protein standard with the size (in kD) of each known protein indicated on the left.

Only cell extracts from IPTG-induced cultures containing pTirt#16 showed a prominent protein band when analyzed by polyacrylamide gel electrophoresis (SDS-PAGE). The expressed protein appeared to be about 48 kilodaltons (kD) in size, according to its migration during electrophoresis in a polyacrylamide protein gel (FIG. 3, lane 4). This was approximately the size expected (52 kD) for the predicted fusion construction of Tirt in plasmid pTirt#16. In addition, Western blot analysis with a specific antibody probe confirmed the presence of a polyhistidine tag in the 48 kD protein band. Most of the expressed fusion protein fractionated into the insoluble cell debris after high speed centrifugation of the cell extract (FIG. 3, lane 9). However, some of the 48 kD fusion protein also appeared in the soluble cell fraction (FIG. 3, lane 8) and the inventors suspected that his fraction might have detectable RT activity. The 48 kD fusion protein was purified from the soluble cell fraction by nickel ion affinity chromatography. A single-step elution of the polyhistidine-tagged fusion protein yielded a partially purified fraction containing predominately a 48 kD protein band (FIG. 4, lanes 6-9, indicated by arrow). Each eluted column fraction was dialyzed and concentrated into a new buffer (buffer A) to stabilize the purified protein (FIG. 4, lanes 11-14). The polyhistidine tag at the N-terminus of the purified Tirt protein was not removed because this short extension of the protein was not expected to affect the RT activity of the fusion protein, since it does not affect the expression of mammalian viral RTs and other recombinant eukaryotic RTs in *E. coli* when similar technology is used for their expression.

EXAMPLE 3

Demonstration of Tirt's Reverse Transcriptase Activity

Figure 5:
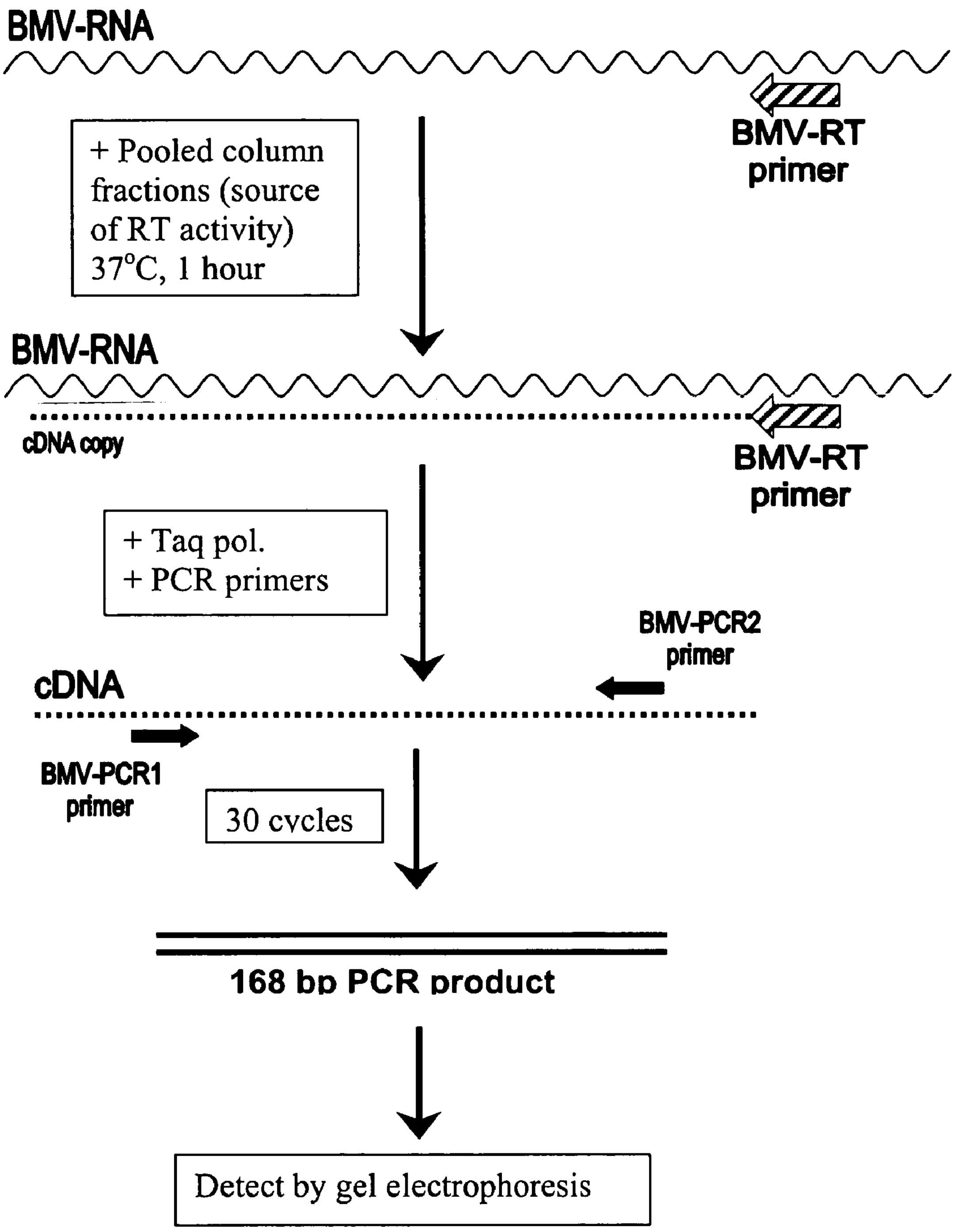
FIG. 5. is a schematic diagram showing the steps involved in the PERT assay used to detect RT activity from cell fractions. Column purified fractions of the Tirt protein serve as a source of RT activity and are added to a reaction mix containing BMV-RNA as a template. Using a specific primer (BMV-RT primer) the activity of the Tirt protein synthesizes a cDNA copy of the BMV-RNA template. A small region of the cDNA copy is then amplified (using specific primers) by the PCR to produce a final amplified product of 168 bp.

Column fractions containing the purified Tirt fusion protein were pooled, dialyzed into buffer A (50 mM Tris-pH 7.5, 1 mM EDTA, 1 mM DTT, and 10% glycerol) using a microcon 30 membrane concentrator (Amicon, Beverly, Mass.), and then used to assay for RT activity. A highly sensitive product enhanced reverse transcriptase (PERT) assay was used to detect RT activity. The assay required the reverse transcription of a Brome Mosaic virus (BMV) RNA template to produce a small cDNA that was then further amplified by PCR (FIG. 5). Briefly, the assay was performed by first assembling the PCR amplification reaction mix in the bottom of a 0.2 ml tube containing: $MgCl_2$-free PCR buffer, 1× (Promega, Madison, Wis.), 1 μM each BMV-PCR1 primer (5'-CGTGGTTGACACGCAGACCTCTTAC-3') [SEQ ID NO: 9] and BMV-PCR2 primer (5'-TCAACACTGTACGGCACCCGCATTC-3') [SEQ ID NO: 10], 0.8 mM each dNTP, and Taq polymerase (Promega). The RT reaction mix was then assembled on top after sealing the lower PCR reaction mix with a layer of wax using an Ampliwax pellet (PCR-Gem 50, Applied Biosystems, Roche). The RT reaction mix contained: RT buffer (50 mM Tris-pH 8.3, 75 mM KCl, and 10 mM DTT), 2.5 mM $MgCl_2$, 0.17% NP-40, 10 units of RNasin (Promega, Madison, Wis.), 0.8 mM each dNTP, 0.02 μM RT primer (5'-GGTCTCTTTTAGAGATTTACAGTG-3') [SEQ ID NO: 11], 100 ng of Brome Mosaic Virus (BMV) RNA (Promega), and a source of RT. The source of RT added to the reaction was either the purified Tirt fusion protein described above or commercially available Moloney Murine Leukemia Virus RT (MMLV-RT) (2 units). The reaction tube was then placed in a thermocycler under the following conditions: 1 cycle at 37° C. for 1 hour (reverse transcription); 1 cycle at 94° C. for 1 minute; 30 cycles at 94° C. for 15 seconds, 56° C. for 15 seconds, and 72° C. for 15 seconds (amplification); and finally 72° C. for 5 minutes. Amplified DNA was detected by electrophoresis of the reaction mix on a 5% polyacrylamide gel followed by staining with ethidium bromide.

Figure 6:
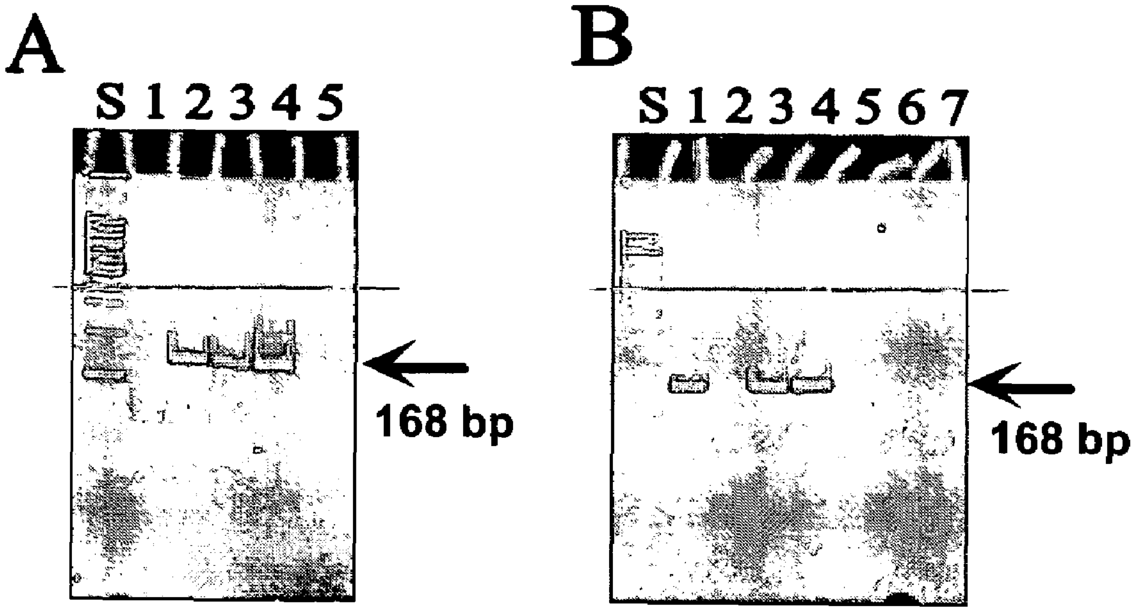
FIG. 6. is a picture of a polyacrylamide gel illustrating the presence of RT activity in a purified preparation of the Tirt fusion protein. Purified preparations of the Tirt protein were added to the PERT assay as a source of RT. Various control reactions were also run with the PERT assay. The production of a 168 bp amplified DNA indicates RT activity. (A): Lane S, 100 bp molecular weight marker; lane 1, affinity purified column fraction #2; lane 2, column fraction #2 after dialysis in buffer A; lane 3, the same as lane 2 but supplemented with MMLV-RT; lane 4, MMLV-RT in RT buffer (serving as a positive control); lane 5, MMLV-RT but with one of the PCR primers absent from the reaction (a negative control). (B): Lane S, 100 bp molecular weight markers; lanes 1-3 contain column fractions # 2-4 respectively after dialysis in buffer A; lane 4, MMLV-RT in RT buffer (positive control); lane 5, MMLV-RT plus RNase A added to the reaction; lane 6, no exogenous ($H_2O$) source of RT added to the reaction; lane 7, column fraction #2 (dialyzed in buffer A) plus RNase A.

The presence of a 168 base pair (bp) PCR product in a DNA gel, following electrophoresis, indicated the presence of RT activity. The assay was run on both crude cell extracts, as well as purified column fractions. No RT activity was detected in the crude cell extracts tested. Furthermore, no RT activity was detected in the purified fractions eluted from the nickel ion affinity column used to purify the fusion protein (FIG. 6A, lane 1). However, when the eluted column fractions were dialyzed and concentrated into buffer A, RT activity was detected in some of the column fractions (FIG. 6B, lanes 1-3), indicating the presence of inhibitors of RT activity in the fractions prior to dialysis. As an additional indication that inhibitors of RT activity are present in the column fractions prior to dialysis, when commercially prepared MMLV-RT was added to the PERT assay, as expected, a 168 bp DNA was produced indicating RT activity (FIG. 6A, lane 4). However, when MMLV-RT was mixed with column fraction #7, no RT activity was detected.

When one of the PCR primers was omitted from the PERT assay, no DNA product was produced (FIG. 6A: lane 4, two primers; lane 5, one primer). This indicated that the 168 bp DNA product was the result of specific amplification of the reverse transcribed cDNA and not some other process. In another control reaction, RNase was added to the fraction to be tested for RT activity. When RNase was mixed with dialyzed column fraction number 2, no DNA product was observed (FIG. 6B lane 1, without RNase; lane 7, RNase added), indicating that the 168 bp DNA was amplified from a cDNA that was reversed transcribed from the BMV RNA template present in the assay and not from contaminating DNA carried over from previous assay reactions. A third control reaction contained only water as the sample extract to be tested for RT activity (FIG. 6B, lane 6). As expected, no DNA product was produced. This confirmed that an exogenous source of RT added to the assay reaction, and not the Taq polymerase present in the assay, was responsible for cDNA formation (and thus the amplification of the 168 bp DNA).

EXAMPLE 4

Demonstration of Heat Stability of Tirt

The column purified Tirt fusion protein (as described above) was added (15 μl) to a microfuge tube and heated in a water bath at either 65° C. or 75° C. for 15 minutes. After heat treatment, the tube was centrifuged and 7.5 μl of the supernatant was added directly to the PERT assay reaction. MMLV-RT diluted in 1×RT buffer (5 units) was treated in a similar fashion.

To run the PERT assay at different temperatures, the reverse transcription reaction was incubated separately at either 37° C., 50° C. or 68° C. After 1 hour of incubation the reaction mix was immediately added to the top of the PCR reaction mix, sealed with a layer of wax, and processed as described in Example 3.

Figure 7:
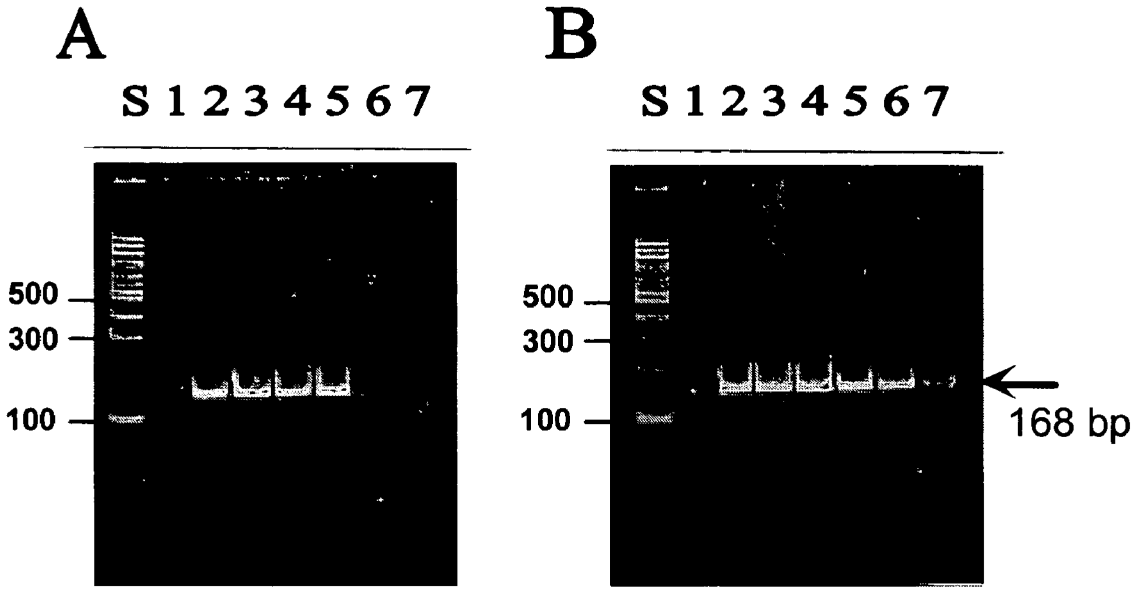
FIG. 7. is a picture of a polyacrylamide gel illustrating the presence of heat stable RT activity associated with purified Tirt protein. The PERT assay was used to detect RT activity of the purified Tirt protein under various temperature conditions. (A) Column purified fractions of Tirt (dialyzed in buffer A) were pooled and incubated at the indicated temperatures for 15 minutes, then added to the PERT assay. Lane S, 100 bp molecular weight marker; lane 1, MMLV-RT with one PCR primer missing (negative control); lane 2, purified Tirt protein with no heat treatment; lane 3, purified Tirt protein heated to 65° C.; lane 4, purified Tirt protein heated to 75° C.; lane 5, commercial preparation of MMLV-RT with no heat treatment; lane 6, MMLV-RT heated to 65° C.; lane 7, MMLV-RT heated to 75° C. (B) The PERT assay itself was run at three different temperatures with either the purified Tirt protein or MMLV-RT added as a source of RT. Lane S, 100 bp molecular weight marker; lane 1, a control reaction containing purified Tirt, but no RNA template was added (negative control); lanes 2-4, is the PERT assay containing the purified Tirt protein incubated at 37° C., 50° C. and 68° C. respectively; lanes 5-7, is the PERT assay containing MMLV-RT incubated at 37° C., 50° C., and 68° C. respectively.

The column-purified Tirt fusion protein was not heated (FIG. 7A, lane 2), heated at 65° C. for 15 minutes (FIG. 7A, lane 3), or heated at 75° C. for 15 minutes (FIG. 7A, lane 4). After heat treatment the purified fraction was tested for RT activity using the PERT assay. As a control, the same procedure was followed using commercially prepared Moloney Murine Leukemia Virus reverse transcriptase (M-MLV-RT). The purified Tirt protein was not reduced in RT activity even after exposure to temperatures of 75° C. (FIG. 7A, lane 4). In contrast, no RT activity was detected after heat treatment (both at 65° C. and 75° C.) of the mesophilic MMLV-RT (FIG. 7A, lanes 6 and 7).

The purified Tirt protein was also tested for RT activity by running the PERT assay at three different temperatures; 37° C., 50° C., and 68° C. (FIG. 7B). Again, the purified Tirt protein was not affected in its ability to synthesize cDNA by reverse transcription even at the highest temperature tested, 68° C. (FIG. 7B, lanes 2 and 4). By contrast, cDNA production appeared to be greatly reduced, at least at the highest temperature of 68° C., for the mesophilic mammalian RT (compare FIG. 7B, lane 5 versus lane 7).

Plasmid pTirt# 16 (comprising vector pET28a from *Escherichia coli* with Tirt coding sequence from *Geobacillus stearothermophilus* inserted) was deposited, prior to the date of filing of this application, with the American Type Culture Collection, Manassas, Va., USA, under the terms of the Budapest Treaty. A computer readable sequence listing accompanies this application, and the sequence listing information recorded in computer readable form is identical to the written sequence listing included in the application papers.

What is claimed is:

1. A substantially purified polypeptide, comprising an amino acid sequence selected from the group consisting of:

a) SEQ ID NO: 2, and b) a variant of SEQ ID NO: 2 having at least 90% sequence identity to SEQ ID NO: 2, the variant having similar reverse transcriptase activity as that of a polypeptide comprising SEQ ID NO: 2.

2. A composition comprising the polypeptide of claim 1 and a carrier.

3. A kit for performing RT-PCR, the kit comprising—at least one aliquot of a substantially purified protein selected from the group consisting of:

a) a polypeptide comprising the amino acid sequence of SEQ ID NO: 2, and b) a polypeptide variant of SEQ ID NO: 2 having at least 90% sequence identity to SEQ ID NO: 2 the variant having similar reverse transcriptase activity as that of a polypeptide comprising SEQ ID NO: 2.

4. The kit of claim 3 further comprising at least one reaction buffer.

5. The kit of claim 3 further comprising at least one aliquot of an RNase inhibitor.

6. The kit of claim 3 further comprising at least one aliquot of a DNA polymerase.

7. The kit of claim 6 wherein the DNA polymerase is Taq polymerase.

8. A method of synthesizing a cDNA copy of an mRNA template, the method comprising:

(a) hybridizing a primer to a first mRNA molecule; and (b) incubating said mRNA molecule of step (a) in the presence of one or more deoxy- or dideoxy ribonucleoside triphosphates and the polypeptide of claim 1, under conditions sufficient to synthesize a cDNA molecule complementary to all or a portion of the first mRNA molecule.

9. The method of claim 8 wherein the primer is an oligo d(T) primer.

10. A substantially purified polypeptide as in claim 1, wherein the variant of SEQ ID NO: 2 has at least 95% sequence identity to SEQ ID NO: 2.

11. A substantially purified polypeptide as in claim 1, wherein the variant of SEQ ID NO: 2 has at least 97% sequence identity to SEQ ID NO: 2.

* * * * *

SEQUENCE LISTING

<160> NUMBER OF SEQ ID NOS: 18

<210> SEQ ID NO 1
<211> LENGTH: 1263
<212> TYPE: DNA
<213> ORGANISM: Geobacillus stearothermophilus
<220> FEATURE:
<221> NAME/KEY: CDS
<222> LOCATION: (1)..(1263)

<400> SEQUENCE: 1 atg gct ttg ttg gaa cgc atc tta gcg aga gac aac ctc atc acg gcg 48
Met Ala Leu Leu Glu Arg Ile Leu Ala Arg Asp Asn Leu Ile Thr Ala
1 5 10 15 ctc aaa cgg gtc gaa gcc aac caa gga gca ccg gga atc gac gga gta 96
Leu Lys Arg Val Glu Ala Asn Gln Gly Ala Pro Gly Ile Asp Gly Val
20 25 30 tca acc gat caa ctc cgt gat tac atc cgc gct cac tgg agc acg atc 144
Ser Thr Asp Gln Leu Arg Asp Tyr Ile Arg Ala His Trp Ser Thr Ile
35 40 45 cgc gcc caa ctc ttg gcg gga acc tac cgg ccg gcg cct gtc cgc agg 192
Arg Ala Gln Leu Leu Ala Gly Thr Tyr Arg Pro Ala Pro Val Arg Arg
50 55 60 gtc gga atc ccg aaa ccg ggc ggc ggc aca cgg cag cta ggc att ccc 240
Val Gly Ile Pro Lys Pro Gly Gly Gly Thr Arg Gln Leu Gly Ile Pro
65 70 75 80 acc gtg gtg gac cgg ctg atc caa caa gcc att ctt caa gaa ctc aca 288
Thr Val Val Asp Arg Leu Ile Gln Gln Ala Ile Leu Gln Glu Leu Thr
85 90 95 ccc att ttc gat cca gac ttc tcc cct tcc agc ttc gga ttc cgt ccg 336
Pro Ile Phe Asp Pro Asp Phe Ser Pro Ser Ser Phe Gly Phe Arg Pro
100 105 110 ggc cgt aac gcc cac gat gcc gtg cgg caa gcg caa ggc tac atc cag 384
Gly Arg Asn Ala His Asp Ala Val Arg Gln Ala Gln Gly Tyr Ile Gln
115 120 125 gaa ggg tat cgg tac gtg gtc gac atg gac ctg gaa aag ttc ttt gat 432
Glu Gly Tyr Arg Tyr Val Val Asp Met Asp Leu Glu Lys Phe Phe Asp
130 135 140 cgg gtc aac cat gac atc ttg atg agt cgg gtg gcc cga aaa gtc aag 480
Arg Val Asn His Asp Ile Leu Met Ser Arg Val Ala Arg Lys Val Lys
145 150 155 160 gat aaa cgc gtg ctg aaa ctg atc cgt gcc tac ctg caa gcc ggc gtt 528
Asp Lys Arg Val Leu Lys Leu Ile Arg Ala Tyr Leu Gln Ala Gly Val
165 170 175 atg atc gaa ggg gtg aag gtg cag acg gag gaa ggg acg ccg caa ggc 576
Met Ile Glu Gly Val Lys Val Gln Thr Glu Glu Gly Thr Pro Gln Gly
180 185 190 ggc ccc ctc agc ccc ctg ctg gcg aac atc ctt ctc gac gat tta gac 624
Gly Pro Leu Ser Pro Leu Leu Ala Asn Ile Leu Leu Asp Asp Leu Asp
195 200 205 aag gaa ttg gag aag cga gga ttg aaa ttc tgc cgt tac gca gat gac 672
Lys Glu Leu Glu Lys Arg Gly Leu Lys Phe Cys Arg Tyr Ala Asp Asp
210 215 220 tgc aac atc tat gtg aaa agt ctg cgg gca gga caa cgg gtg aaa caa 720
Cys Asn Ile Tyr Val Lys Ser Leu Arg Ala Gly Gln Arg Val Lys Gln
225 230 235 240 agc atc caa cgg ttc ttg gag aaa acg ctc aaa ctc aaa gta aac gag 768
Ser Ile Gln Arg Phe Leu Glu Lys Thr Leu Lys Leu Lys Val Asn Glu
245 250 255

-continued

```
gag aaa agt gcg gtg gac cgc ccg tgg aaa cgg gcc ttt ctg ggg ttt      816
Glu Lys Ser Ala Val Asp Arg Pro Trp Lys Arg Ala Phe Leu Gly Phe
            260                 265                 270

agc ttc aca ccg gaa cga aaa gcg cga atc cgg ctc gcc cca agg tcg      864
Ser Phe Thr Pro Glu Arg Lys Ala Arg Ile Arg Leu Ala Pro Arg Ser
        275                 280                 285

att caa cgt ctg aaa cag cgg att cga cag ctg acc aac cca aac tgg      912
Ile Gln Arg Leu Lys Gln Arg Ile Arg Gln Leu Thr Asn Pro Asn Trp
    290                 295                 300

agc ata tcg atg cca gaa cga att cat cgc gtc aat caa tac gtc atg      960
Ser Ile Ser Met Pro Glu Arg Ile His Arg Val Asn Gln Tyr Val Met
305                 310                 315                 320

gga tgg atc ggg tat ttt cgg ctc gtc gaa acc ccg tct gtc ctt cag     1008
Gly Trp Ile Gly Tyr Phe Arg Leu Val Glu Thr Pro Ser Val Leu Gln
                325                 330                 335

acc atc gaa gga tgg att cgg agg agg ctt cga ctc tgt caa tgg ctt     1056
Thr Ile Glu Gly Trp Ile Arg Arg Arg Leu Arg Leu Cys Gln Trp Leu
            340                 345                 350

caa tgg aaa cgg gtc aga acc aga atc cgt gag tta aga gcg ctg ggg     1104
Gln Trp Lys Arg Val Arg Thr Arg Ile Arg Glu Leu Arg Ala Leu Gly
        355                 360                 365

ctg aaa gag aca gcg gtg atg gag atc gcc aat acc cga aaa gga gct     1152
Leu Lys Glu Thr Ala Val Met Glu Ile Ala Asn Thr Arg Lys Gly Ala
    370                 375                 380

tgg cga aca acg aaa acg ccg caa ctc cac cag gcc ctg ggc aaa acc     1200
Trp Arg Thr Thr Lys Thr Pro Gln Leu His Gln Ala Leu Gly Lys Thr
385                 390                 395                 400

tac tgg acc gct caa ggg ctc aag agt ttg acg caa cga tat ttc gaa     1248
Tyr Trp Thr Ala Gln Gly Leu Lys Ser Leu Thr Gln Arg Tyr Phe Glu
                405                 410                 415

ctc cgt caa ggt tga                                                 1263
Leu Arg Gln Gly
            420


<210> SEQ ID NO 2
<211> LENGTH: 420
<212> TYPE: PRT
<213> ORGANISM: Geobacillus stearothermophilus

<400> SEQUENCE: 2

Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
            20                  25                  30

Ser Thr Asp Gln Leu Arg Asp Tyr Ile Arg Ala His Trp Ser Thr Ile
        35                  40                  45

Arg Ala Gln Leu Leu Ala Gly Thr Tyr Arg Pro Ala Pro Val Arg Arg
    50                  55                  60

Val Gly Ile Pro Lys Pro Gly Gly Gly Thr Arg Gln Leu Gly Ile Pro
65                  70                  75                  80

Thr Val Val Asp Arg Leu Ile Gln Gln Ala Ile Leu Gln Glu Leu Thr
                85                  90                  95

Pro Ile Phe Asp Pro Asp Phe Ser Pro Ser Ser Phe Gly Phe Arg Pro
            100                 105                 110

Gly Arg Asn Ala His Asp Ala Val Arg Gln Ala Gln Gly Tyr Ile Gln
        115                 120                 125

Glu Gly Tyr Arg Tyr Val Val Asp Met Asp Leu Glu Lys Phe Phe Asp
    130                 135                 140
```

-continued

```
Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Glu Gly Thr Pro Gln Gly
            180                 185                 190

Gly Pro Leu Ser Pro Leu Leu Ala Asn Ile Leu Leu Asp Asp Leu Asp
        195                 200                 205

Lys Glu Leu Glu Lys Arg Gly Leu Lys Phe Cys Arg Tyr Ala Asp Asp
    210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300

Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335

Thr Ile Glu Gly Trp Ile Arg Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365

Leu Lys Glu Thr Ala Val Met Glu Ile Ala Asn Thr Arg Lys Gly Ala
    370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420


<210> SEQ ID NO 3
<211> LENGTH: 420
<212> TYPE: PRT
<213> ORGANISM: Geobacillus stearothermophilus
<220> FEATURE:
<221> NAME/KEY: PEPTIDE
<222> LOCATION: (1)..(420)

<400> SEQUENCE: 3

Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
            20                  25                  30

Ser Thr Asp Gln Leu Arg Asp Tyr Ile Arg Ala His Trp Ser Thr Ile
        35                  40                  45

Arg Ala Gln Leu Leu Ala Gly Thr Tyr Arg Pro Ala Pro Val Arg Arg
    50                  55                  60

Val Gly Ile Pro Lys Pro Gly Gly Gly Thr Arg Gln Leu Gly Ile Pro
65                  70                  75                  80
```

-continued

```
Thr Val Val Asp Arg Leu Ile Gln Gln Ala Ile Leu Gln Glu Leu Thr
                85                  90                  95

Pro Ile Phe Asp Pro Asp Phe Ser Pro Ser Ser Phe Gly Phe Arg Pro
            100                 105                 110

Gly Arg Asn Ala His Asp Ala Val Arg Gln Ala Gln Gly Tyr Ile Gln
        115                 120                 125

Glu Gly Tyr Arg Tyr Val Val Asp Met Asp Leu Glu Lys Phe Phe Asp
    130                 135                 140

Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Glu Gly Thr Pro Gln Gly
            180                 185                 190

Gly Pro Leu Ser Pro Leu Leu Ala Asn Ile Leu Leu Asp Asp Leu Asp
        195                 200                 205

Lys Glu Leu Glu Lys Arg Gly Leu Lys Phe Cys Arg Tyr Ala Asp Asp
    210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300

Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335

Thr Ile Glu Gly Trp Ile Arg Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365

Leu Lys Glu Thr Ala Val Met Glu Ile Ala Asn Thr Arg Lys Gly Ala
    370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420
```

<210> SEQ ID NO 4
<211> LENGTH: 1370
<212> TYPE: DNA
<213> ORGANISM: Artificial
<220> FEATURE:
<223> OTHER INFORMATION: Plasmid construct
<220> FEATURE:
<221> NAME/KEY: misc_feature
<222> LOCATION: (1)..(1370)

<400> SEQUENCE: 4

-continued ccatgggcag cagccatcat catcatcatc acagcagcgg cctggtgccg cgcggcagcc 60
atatgcggca agacctgaat ctcatcccgc ggaaggagaa gatcacgatg gctttgttgg 120
aacgcatctt agcgagagac aacctcatca cggcgctcaa acgggtcgaa gccaaccaag 180
gagcaccggg aatcgacgga gtatcaaccg atcaactccg tgattacatc cgcgctcact 240
ggagcacgat ccgcgcccaa ctcttggcgg gaacctaccg gccggcgcct gtccgcaggg 300
tcggaatccc gaaaccgggc ggcggcacac ggcagctagg cattcccacc gtggtggacc 360
ggctgatcca acaagccatt cttcaagaac tcacacccat tttcgatcca gacttctccc 420
cttccagctt cggattccgt ccgggccgta acgcccacga tgccgtgcgg caagcgcaag 480
gctacatcca ggaagggtat cggtacgtgg tcgacatgga cctggaaaag ttctttgatc 540
gggtcaacca tgacatcttg atgagtcggg tggcccgaaa agtcaaggat aaacgcgtgc 600
tgaaactgat ccgtgcctac ctgcaagccg gcgttatgat cgaaggggtg aaggtgcaga 660
cggaggaagg gacgccgcaa ggcggccccc tcagccccct gctggcgaac atccttctcg 720
acgatttaga caaggaattg gagaagcgag gattgaaatt ctgccgttac gcagatgact 780
gcaacatcta tgtgaaaagt ctgcgggcag gacaacgggt gaaacaaagc atccaacggt 840
tcttggagaa aacgctcaaa ctcaaagtaa acgaggagaa aagtgcggtg gaccgcccgt 900
ggaaacgggc ctttctgggg tttagcttca caccggaacg aaaagcgcga atccggctcg 960
ccccaaggtc gattcaacgt ctgaaacagc ggattcgaca gctgaccaac ccaaactgga 1020
gcatatcgat gccagaacga attcatcgcg tcaatcaata cgtcatggga tggatcgggt 1080
attttcggct cgtcgaaacc ccgtctgtcc ttcagaccat cgaaggatgg attcggagga 1140
ggcttcgact ctgtcaatgg cttcaatgga aacgggtcag aaccagaatc cgtgagttaa 1200
gagcgctggg gctgaaagag acagcggtga tggagatcgc caatacccga aaaggagctt 1260
ggcgaacaac gaaaacgccg caactccacc aggccctggg caaaacctac tggaccgctc 1320
aagggctcaa gagtttgacg caacgatatt tcgaactccg tcaaggttga 1370

<210> SEQ ID NO 5
<211> LENGTH: 32
<212> TYPE: DNA
<213> ORGANISM: Artificial
<220> FEATURE:
<223> OTHER INFORMATION: Nucleotide primer containing NdeI restriction site
<220> FEATURE:
<221> NAME/KEY: primer_bind
<222> LOCATION: (1)..(32)

<400> SEQUENCE: 5
agacaacata tgcggcaaga cctgaatctc at 32

<210> SEQ ID NO 6
<211> LENGTH: 28
<212> TYPE: DNA
<213> ORGANISM: Artificial
<220> FEATURE:
<223> OTHER INFORMATION: Nucleotide primer containing BamHI restriction site

<400> SEQUENCE: 6
aatggatccg ctggcgaaca tccttctc 28

<210> SEQ ID NO 7
<211> LENGTH: 29

-continued

<212> TYPE: DNA
<213> ORGANISM: Artificial
<220> FEATURE:
<223> OTHER INFORMATION: Nucleotide primer containing PstI restriction site
<220> FEATURE:
<221> NAME/KEY: primer_bind
<222> LOCATION: (1)..(29)

<400> SEQUENCE: 7
attactgcag agcggtccag taggttttg 29

<210> SEQ ID NO 8
<211> LENGTH: 31
<212> TYPE: DNA
<213> ORGANISM: Artificial
<220> FEATURE:
<223> OTHER INFORMATION: Nucleotide primer containing HindIII restriction site
<220> FEATURE:
<221> NAME/KEY: primer_bind
<222> LOCATION: (1)..(31)

<400> SEQUENCE: 8
actcaagctt gagaagggct tgacgttcat g 31

<210> SEQ ID NO 9
<211> LENGTH: 455
<212> TYPE: PRT
<213> ORGANISM: Artificial
<220> FEATURE:
<223> OTHER INFORMATION: Amino acid sequence of fusion protein
<220> FEATURE:
<221> NAME/KEY: Plasmid
<222> LOCATION: (1)..(455)
<220> FEATURE:
<221> NAME/KEY: PEPTIDE
<222> LOCATION: (1)..(455)

<400> SEQUENCE: 9

```
Met Gly Ser Ser His His His His His His Ser Ser Gly Leu Val Pro
1               5                   10                  15

Arg Gly Ser His Met Arg Gln Asp Leu Asn Leu Ile Pro Arg Lys Glu
            20                  25                  30

Lys Ile Thr Met Ala Leu Leu Glu Arg Ile Leu Ala Arg Asp Asn Leu
        35                  40                  45

Ile Thr Ala Leu Lys Arg Val Glu Ala Asn Gln Gly Ala Pro Gly Ile
    50                  55                  60

Asp Gly Val Ser Thr Asp Gln Leu Arg Asp Tyr Ile Arg Ala His Trp
65                  70                  75                  80

Ser Thr Ile Arg Ala Gln Leu Leu Ala Gly Thr Tyr Arg Pro Ala Pro
                85                  90                  95

Val Arg Arg Val Gly Ile Pro Lys Pro Gly Gly Gly Thr Arg Gln Leu
            100                 105                 110

Gly Ile Pro Thr Val Val Asp Arg Leu Ile Gln Gln Ala Ile Leu Gln
        115                 120                 125

Glu Leu Thr Pro Ile Phe Asp Pro Asp Phe Ser Pro Ser Ser Phe Gly
    130                 135                 140

Phe Arg Pro Gly Arg Asn Ala His Asp Ala Val Arg Gln Ala Gln Gly
145                 150                 155                 160

Tyr Ile Gln Glu Gly Tyr Arg Tyr Val Val Asp Met Asp Leu Glu Lys
                165                 170                 175

Phe Phe Asp Arg Val Asn His Asp Ile Leu Met Ser Arg Val Ala Arg
```

-continued

```
            180                 185                 190

Lys Val Lys Asp Lys Arg Val Leu Lys Leu Ile Arg Ala Tyr Leu Gln
        195                 200                 205

Ala Gly Val Met Ile Glu Gly Val Lys Val Gln Thr Glu Glu Gly Thr
    210                 215                 220

Pro Gln Gly Gly Pro Leu Ser Pro Leu Leu Ala Asn Ile Leu Leu Asp
225                 230                 235                 240

Asp Leu Asp Lys Glu Leu Glu Lys Arg Gly Leu Lys Phe Cys Arg Tyr
                245                 250                 255

Ala Asp Asp Cys Asn Ile Tyr Val Lys Ser Leu Arg Ala Gly Gln Arg
            260                 265                 270

Val Lys Gln Ser Ile Gln Arg Phe Leu Glu Lys Thr Leu Lys Leu Lys
        275                 280                 285

Val Asn Glu Glu Lys Ser Ala Val Asp Arg Pro Trp Lys Arg Ala Phe
    290                 295                 300

Leu Gly Phe Ser Phe Thr Pro Glu Arg Lys Ala Arg Ile Arg Leu Ala
305                 310                 315                 320

Pro Arg Ser Ile Gln Arg Leu Lys Gln Arg Ile Arg Gln Leu Thr Asn
                325                 330                 335

Pro Asn Trp Ser Ile Ser Met Pro Glu Arg Ile His Arg Val Asn Gln
            340                 345                 350

Tyr Val Met Gly Trp Ile Gly Tyr Phe Arg Leu Val Glu Thr Pro Ser
        355                 360                 365

Val Leu Gln Thr Ile Glu Gly Trp Ile Arg Arg Arg Leu Arg Leu Cys
    370                 375                 380

Gln Trp Leu Gln Trp Lys Arg Val Arg Thr Arg Ile Arg Glu Leu Arg
385                 390                 395                 400

Ala Leu Gly Leu Lys Glu Thr Ala Val Met Glu Ile Ala Asn Thr Arg
                405                 410                 415

Lys Gly Ala Trp Arg Thr Thr Lys Thr Pro Gln Leu His Gln Ala Leu
            420                 425                 430

Gly Lys Thr Tyr Trp Thr Ala Gln Gly Leu Lys Ser Leu Thr Gln Arg
        435                 440                 445

Tyr Phe Glu Leu Arg Gln Gly
    450                 455
```

<210> SEQ ID NO 10
<211> LENGTH: 25
<212> TYPE: DNA
<213> ORGANISM: Artificial
<220> FEATURE:
<223> OTHER INFORMATION: Primer sequence
<220> FEATURE:
<221> NAME/KEY: prim_transcript
<222> LOCATION: (1)..(25)

<400> SEQUENCE: 10
cgtggttgac acgcagacct cttac 25

<210> SEQ ID NO 11
<211> LENGTH: 25
<212> TYPE: DNA
<213> ORGANISM: Artificial
<220> FEATURE:
<223> OTHER INFORMATION: Primer sequence
<220> FEATURE:
<221> NAME/KEY: prim_transcript
<222> LOCATION: (1)..(25)

-continued

<400> SEQUENCE: 11
tcaacactgt acggcacccg cattc 25

<210> SEQ ID NO 12
<211> LENGTH: 24
<212> TYPE: DNA
<213> ORGANISM: Artificial
<220> FEATURE:
<223> OTHER INFORMATION: Primer sequence
<220> FEATURE:
<221> NAME/KEY: prim_transcript
<222> LOCATION: (1)..(24)

<400> SEQUENCE: 12
ggtctctttt agagatttac agtg 24

<210> SEQ ID NO 13
<211> LENGTH: 394
<212> TYPE: PRT
<213> ORGANISM: Bacillus halodurans
<220> FEATURE:
<221> NAME/KEY: PEPTIDE
<222> LOCATION: (1)..(394)

<400> SEQUENCE: 13

```
Met Leu Glu Arg Ile Leu Ser Arg Glu Asn Leu Ile Gln Leu Glu Arg
1               5                   10                  15

Val Glu Lys Asn Lys Gly Ser Tyr Gly Val Asp Glu Met Asp Val Lys
            20                  25                  30

Ser Leu Arg Leu His Leu His Glu Asn Trp Thr Ser Ile Arg Asn Glu
        35                  40                  45

Ile Ile Glu Gly Ser Tyr Phe Pro Lys Pro Val Arg Arg Val Glu Ile
    50                  55                  60

Pro Lys Pro Asn Gly Gly Val Arg Lys Leu Gly Ile Pro Thr Val Met
65                  70                  75                  80

Asp Arg Phe Leu Gln Gln Ala Ile Ala Gln Ile Leu Thr Gln Leu Tyr
                85                  90                  95

Asp Pro Thr Phe Ser Glu Arg Ser Phe Gly Phe Arg Pro His Arg Arg
            100                 105                 110

Gly His Asn Ala Val Arg Gln Ala Lys Gln Trp Met Lys Glu Gly Tyr
        115                 120                 125

Arg Trp Val Val Asp Ile Asp Leu Glu Lys Phe Phe Asp Lys Val Asn
    130                 135                 140

His Asp Arg Leu Met Arg Lys Leu Ser Ser Arg Ile Gln Asp Pro Arg
145                 150                 155                 160

Val Leu Gly Leu Ile Arg Arg Tyr Leu Gln Thr Gly Val Met Glu Arg
                165                 170                 175

Gly Leu Val Ser Pro Asn Thr Glu Gly Thr Pro Gln Gly Gly Pro Leu
            180                 185                 190

Ser Pro Leu Leu Ser Asn Ile Val Leu Asp Glu Leu Asp Asn Glu Leu
        195                 200                 205

Glu Lys Arg Gly Leu Lys Phe Val Arg Tyr Ala Asp Asp Cys Asn Ile
    210                 215                 220

Tyr Val Arg Ser Lys Arg Ala Gly Leu Arg Ile Met Glu Ser Val Thr
225                 230                 235                 240

Ser Phe Ile Glu Asn Arg Leu Lys Leu Lys Val Asn Arg Glu Lys Ser
                245                 250                 255

Ala Val Asp Arg Pro Trp Asn Arg Lys Phe Leu Gly Phe Ser Phe Thr
```

-continued

```
            260                 265                 270

Arg Gly Lys Asp Pro Lys Met Arg Val Ser Lys Glu Ser Val Lys Arg
        275                 280                 285

Leu Lys Gln Arg Ile Arg Glu Leu Thr Ser Arg Arg His Ser Met Lys
    290                 295                 300

Met Ser Asp Arg Leu Arg Arg Leu Asn Arg Tyr Leu Thr Gly Trp Leu
305                 310                 315                 320

Gly Tyr Tyr Gln Val Val Asp Thr Pro Ser Ile Leu Ala Gln Ile Asp
                325                 330                 335

Ala Trp Ile Arg Arg Arg Leu Arg Met Ile Arg Trp Lys Glu Trp Lys
            340                 345                 350

Thr Thr Ser Ala Arg Gln Lys Asn Leu Val Arg Leu Gly Ile Lys Lys
        355                 360                 365

Ala Lys Ala Trp Gln Trp Ala Asn Ser Arg Lys Gly Tyr Trp Arg Val
    370                 375                 380

Ala His Ser Pro Ile Met Asp Tyr Ala Leu
385                 390


<210> SEQ ID NO 14
<211> LENGTH: 449
<212> TYPE: PRT
<213> ORGANISM: Clostridium acetobutylicum
<220> FEATURE:
<221> NAME/KEY: PEPTIDE
<222> LOCATION: (1)..(449)

<400> SEQUENCE: 14

Met Lys Asn Ser Lys Glu Met Gln Lys Leu Gln Thr Thr Ser Tyr Lys
1               5                   10                  15

Glu Gly Trp Ser Cys Glu Ile Arg Val Glu Leu Gln Asn Ser Thr Arg
            20                  25                  30

Ala His Ser Ile Ser Thr Ala Phe Asp Arg Arg Lys Asp Asp Gly Lys
        35                  40                  45

Leu Tyr Glu Thr Asn Leu Leu Glu Arg Ile Leu Asp Arg Gln Asn Met
    50                  55                  60

Asn Leu Ala Tyr Lys Arg Val Lys Ser Asn Lys Gly Ser His Gly Val
65                  70                  75                  80

Asp Gly Met Lys Val Asp Glu Leu Leu Gln Tyr Leu Lys Gln Asn Gly
                85                  90                  95

Lys Thr Leu Ile Ala Ser Ile Phe Asn Gly Lys Tyr Cys Pro Lys Ala
            100                 105                 110

Val Arg Arg Val Glu Ile Pro Lys Pro Asp Gly Gly Ile Arg Leu Leu
        115                 120                 125

Gly Ile Pro Thr Val Val Asp Arg Thr Ile Gln Gln Ala Ile Ser Gln
    130                 135                 140

Val Leu Thr Pro Ile Phe Glu Lys Thr Phe Ser Glu Asn Ser Tyr Gly
145                 150                 155                 160

Phe Arg Pro Lys Arg Ser Ala Lys Gln Ala Ile Lys Lys Ala Lys Glu
                165                 170                 175

Tyr Met Glu Glu Gly Tyr Lys Trp Val Val Asp Ile Asp Leu Ala Lys
            180                 185                 190

Tyr Phe Asp Thr Val Asn His Asp Lys Leu Met Ala Leu Val Ala Arg
        195                 200                 205

Lys Ile Lys Asp Lys Arg Val Leu Lys Leu Ile Arg Leu Tyr Leu Gln
    210                 215                 220
```

-continued

Ser Gly Val Met Ile Asn Gly Val Val Ser Glu Thr Glu Arg Gly Cys
225 230 235 240

Pro Gln Gly Gly Pro Leu Ser Pro Leu Leu Ser Asn Ile Met Leu Thr
245 250 255

Glu Leu Asp Arg Glu Leu Glu Lys Arg Gly His Lys Phe Cys Arg Tyr
260 265 270

Ala Asp Asp Asn Asn Val Tyr Val Arg Ser Lys Lys Ala Gly Asp Arg
275 280 285

Val Met Arg Ser Ile Thr Arg Phe Ile Glu Asn Lys Leu Lys Leu Lys
290 295 300

Val Asn Lys Glu Lys Ser Ala Val Asp Arg Pro Trp Arg Arg Lys Phe
305 310 315 320

Leu Gly Phe Thr Phe Tyr Gln Trp Tyr Gly Lys Ile Gly Ile Arg Val
325 330 335

His Glu Lys Ser Val Lys Lys Phe Lys Ala Lys Ile Lys Ala Ile Thr
340 345 350

Ala Arg Ser Asn Ala Leu Asn Ile Glu Asn Arg Ile Ile Lys Leu Arg
355 360 365

Gln Cys Ile Ile Gly Trp Leu Asn Tyr Phe Gly Ile Ala Glu Met Thr
370 375 380

Lys Leu Ala Lys Lys Leu Asp Glu Trp Thr Arg Arg Arg Leu Arg Met
385 390 395 400

Cys Tyr Trp Lys Gln Trp Lys Lys Val Lys Thr Lys Tyr Asp Asn Leu
405 410 415

Arg Lys Phe Gly Ile Asn Asn Ser Lys Ala Trp Glu Phe Ala Asn Thr
420 425 430

Arg Lys Ser Tyr Trp Arg Ile Ala Asn Ser Pro Ile Leu Ser Thr Thr
435 440 445

Leu

<210> SEQ ID NO 15
<211> LENGTH: 449
<212> TYPE: PRT
<213> ORGANISM: Pseudomonas alcaligenes
<220> FEATURE:
<221> NAME/KEY: PEPTIDE
<222> LOCATION: (1)..(449)

<400> SEQUENCE: 15

Met Pro Pro Val Gly Val Ala Val Ser Leu Val Thr Val Met Gln Lys
1 5 10 15

Phe Pro Thr Ala Glu Thr Val Ile Pro Asn Pro Gly Gln Lys Pro Arg
20 25 30

Val Met Pro Asp Ser Ala Lys Val Pro Ala Ala Ser Ala Thr Trp Thr
35 40 45

Asn Ala Glu Pro Asp Thr Leu Met Glu Arg Val Leu Ala Pro Ala Asn
50 55 60

Leu Arg Arg Ala Tyr Gln Arg Val Val Ser Asn Lys Gly Ala Pro Gly
65 70 75 80

Ala Asp Gly Met Thr Val Ala Asp Leu Ala Gly Tyr Val Lys Gln Tyr
85 90 95

Trp Pro Thr Leu Lys Ala Arg Leu Leu Ala Gly Glu Tyr His Pro Gln
100 105 110

Ala Val Arg Ala Val Glu Ile Pro Lys Pro Gln Gly Gly Thr Arg Gln
115 120 125

-continued

```
Leu Gly Ile Pro Ser Val Val Asp Arg Leu Ile Gln Gln Ala Leu Gln
    130                 135                 140

Gln Gln Leu Thr Pro Ile Phe Asp Pro Leu Phe Ser Lys Tyr Ser Tyr
145                 150                 155                 160

Gly Phe Arg Pro Gly Arg Ser Thr His Gln Ala Ile Glu Met Ala Arg
                165                 170                 175

Ala His Val Thr Ala Gly His Arg Trp Cys Val Glu Leu Asp Leu Glu
            180                 185                 190

Lys Phe Phe Asp Arg Val Asn His Asp Ile Leu Met Ala Cys Ile Glu
        195                 200                 205

Arg Arg Ile Lys Asp Lys Cys Val Leu Arg Leu Ile Arg Arg Tyr Leu
    210                 215                 220

Glu Ala Gly Ile Met Ser Gly Gly Val Val Ser Pro Arg Gln Glu Gly
225                 230                 235                 240

Thr Pro Gln Gly Gly Pro Leu Ser Pro Leu Leu Ser Asn Ile Leu Leu
                245                 250                 255

Asp Glu Leu Asp Arg Glu Leu Glu Arg Arg Gly His Arg Phe Val Arg
            260                 265                 270

Tyr Ala Asp Asp Ala Asn Ile Tyr Val Arg Ser Pro Arg Ala Gly Glu
        275                 280                 285

Arg Val Leu Val Ser Val Glu Arg Phe Leu Arg Glu Arg Leu Lys Leu
    290                 295                 300

Thr Val Asn Arg Lys Lys Ser Gln Val Ala Arg Ala Trp Lys Cys Asp
305                 310                 315                 320

Tyr Leu Gly Tyr Gly Met Ser Trp His Gln Gln Pro Arg Leu Arg Val
                325                 330                 335

Ala Arg Met Ser Leu Asp Arg Leu Arg Asp Arg Leu Arg Met Leu Leu
            340                 345                 350

Arg Ser Val Arg Ala Arg Lys Met Ala Thr Val Ile Glu Arg Ile Asn
        355                 360                 365

Pro Val Leu Arg Gly Trp Ala Ser Tyr Phe Lys Leu Ser Gln Ser Lys
    370                 375                 380

Arg Pro Leu Glu Glu Leu Asp Gly Trp Val Arg His Lys Leu Arg Cys
385                 390                 395                 400

Val Ile Trp Arg Gln Trp Lys Gln Pro Pro Thr Arg Leu Arg Asn Leu
                405                 410                 415

Met Arg Leu Gly Leu Ser Glu Glu Arg Ala Asn Lys Ser Ala Phe Asn
            420                 425                 430

Gly Arg Gly Pro Trp Trp Asn Ser Gly Ala Gln His Met Asn Tyr Ala
        435                 440                 445

Leu


<210> SEQ ID NO 16
<211> LENGTH: 1620
<212> TYPE: DNA
<213> ORGANISM: Geobacillus stearothermophilus
<220> FEATURE:
<221> NAME/KEY: gene
<222> LOCATION: (1)..(1620)

<400> SEQUENCE: 16

gatgttgcgt gtcgaagcag aattcctttc ggaactcatc tgaggaagca agggtgaagc      60

ccagagggcc tcagatcgag ggctgagcgc aacccggcaa gacctgaatc tcatcccgcg     120

gaaggagaag gagaagatca cgatggcttt gttggaacgc atcttagcga gagacaacct     180
```

-continued

```
catcacggcg ctcaaacggg tcgaagccaa ccaaggagca ccgggaatcg acggagtatc    240

aaccgatcaa ctccgtgatt acatccgcgc tcactggagc acgatccgcg cccaactctt    300

ggcgggaacc taccggccgg cgcctgtccg cagggtcgga atcccgaaac cgggcggcgg    360

cacacggcag ctaggcattc ccaccgtggt ggaccggctg atccaacaag ccattcttca    420

agaactcaca cccattttcg atccagactt ctccccttcc agcttcggat tccgtccggg    480

ccgtaacgcc cacgatgccg tgcggcaagc gcaaggctac atccaggaag ggtatcggta    540

cgtggtcgac atggacctgg aaaagttctt tgatcgggtc aaccatgaca tcttgatgag    600

tcgggtggcc cgaaaagtca aggataaacg cgtgctgaaa ctgatccgtg cctacctgca    660

agccggcgtt atgatcgaag ggggtgaaggt gcagacggag gaagggacgc cgcaaggcgg    720

ccccctcagc cccctgctgg cgaacatcct tctcgacgat ttagacaagg aattggagaa    780

gcgaggattg aaattctgcc gttacgcaga tgactgcaac atctatgtga aaagtctgcg    840

ggcaggacaa cgggtgaaac aaagcatcca acggttcttg gagaaaacgc tcaaactcaa    900

agtaaacgag gagaaaagtg cggtggaccg cccgtggaaa cgggcctttc tggggtttag    960

cttcacaccg gaacgaaaag cgcgaatccg gctcgcccca aggtcgattc aacgtctgaa   1020

acagcggatt cgacagctga ccaacccaaa ctggagcata tcgatgccag aacgaattca   1080

tcgcgtcaat caatacgtca tgggatggat cgggtatttt cggctcgtcg aaaccccgtc   1140

tgtccttcag accatcgaag gatggattcg gaggaggctt cgactctgtc aatggcttca   1200

atggaaacgg gtcagaacca gaatccgtga gttaagagcg ctggggctga aagagacagc   1260

ggtgatggag atcgccaata cccgaaaagg agcttggcga acaacgaaaa cgccgcaact   1320

ccaccaggcc ctgggcaaaa cctactggac cgctcaaggg ctcaagagtt tgacgcaacg   1380

atatttcgaa ctccgtcaag gttgacgaac cgcctagtgc ggacccgcat gctaggtggt   1440

gtgaggggac gggggttagc cgccccctcc tactcgattc gtattgtcat tcggcgctat   1500

gccacgcgaa acggccatga acgtcaagcc cttctccttg ttagatcgtc tccttcccgc   1560

gcacgccgtt gatcgaatag ctcgctgtaa tggcggcatt taacgaatgg gaaacggaac   1620
```

<210> SEQ ID NO 17
<211> LENGTH: 299
<212> TYPE: DNA
<213> ORGANISM: Artificial Sequence
<220> FEATURE:
<223> OTHER INFORMATION: Partial DNA sequence of Tirt plasmid #16
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t -continued

```
<400> SEQUENCE: 17

tggnnnnagt ntttaacctt tgnaccgccn taatacnact cactataggg gaattgtgag      60

cggataacaa ttcccctcta gaaataattt tntttaactt taagaaggag atataccatg     120

ggcagcagcc atcatcatca tcatcacagc agcggcctgg tgccgcgcgg cagccatatg     180

cggcaagacc tgaatctcat cccgcggaag gagaagatca cgatggcttt gttggaacgc     240

atcttagcga gagacaacct catcacggcg ctcaaacggg tcgaagccaa ccaaggagc      299


<210> SEQ ID NO 18
<211> LENGTH: 61
<212> TYPE: PRT
<213> ORGANISM: Artificial
<220> FEATURE:
<223> OTHER INFORMATION: Partial amino acid sequence generated from Tirt
      plasmid #16 (pTirt#16)

<400> SEQUENCE: 18

Met Gly Ser Ser His His His His His His Ser Ser Gly Leu Val Pro
1               5                   10                  15

Arg Gly Ser His Met Arg Gln Asp Leu Asn Leu Ile Pro Arg Lys Glu
            20                  25                  30

Lys Ile Thr Met Ala Leu Leu Glu Arg Ile Leu Ala Arg Asp Asn Leu
        35                  40                  45

Ile Thr Ala Leu Lys Arg Val Glu Ala Asn Gln Gly Ala
    50                  55                  60
```